US008803515B2

(12) United States Patent
Goldfine et al.

(10) Patent No.: US 8,803,515 B2
(45) Date of Patent: Aug. 12, 2014

(54) DURABILITY ENHANCED AND REDUNDANT EMBEDDED SENSORS

(75) Inventors: Neil J. Goldfine, Newton, MA (US); David C. Grundy, Chelmsford, MA (US); Darrell E. Schlicker, Freeland, MI (US); Andrew P. Washabaugh, Chula Vista, CA (US)

(73) Assignee: JENTEK Sensors, Inc., Waltham, MA (US)

( * ) Notice: Subject to any disclaimer, the term of this patent is extended or adjusted under 35 U.S.C. 154(b) by 660 days.

(21) Appl. No.: 13/024,154

(22) Filed: Feb. 9, 2011

(65) Prior Publication Data

US 2011/0210724 A1  Sep. 1, 2011

Related U.S. Application Data

(60) Provisional application No. 61/303,033, filed on Feb. 10, 2010.

(51) Int. Cl.
*G01N 27/72* (2006.01)
*G01R 33/14* (2006.01)

(52) U.S. Cl.
USPC ........................................ 324/239; 324/222

(58) Field of Classification Search
USPC ....................................................... 324/239
See application file for complete search history.

(56) References Cited

U.S. PATENT DOCUMENTS

| | | | |
|---|---|---|---|
| 5,831,431 A * | 11/1998 | Gottfried-Gottfried et al. | 324/239 |
| 6,657,429 B1 | 12/2003 | Goldfine et al. | |
| 6,690,164 B1 * | 2/2004 | Fedeli et al. | 324/253 |
| 7,049,811 B2 | 5/2006 | Schlicker et al. | |
| 7,467,057 B2 | 12/2008 | Sheiretov et al. | |
| 7,696,748 B2 | 4/2010 | Schlicker et al. | |
| 2007/0194781 A1 * | 8/2007 | Zhitomirskiy | 324/207.17 |
| 2011/0018532 A1 * | 1/2011 | Florescu et al. | 324/251 |

* cited by examiner

*Primary Examiner* — Bot Ledynh
(74) *Attorney, Agent, or Firm* — Hamilton, Brook, Smith & Reynolds, P.C.

(57) ABSTRACT

A substantially planar eddy-current sensor having durability enhancing pillars in an active region is provided. The pillars are distributed and sized so as to have limited effect on the sensor's performance. When the sensor is mounted on a component such that the sensor experiences forces on a top and bottom surface, the pillars bear the load reducing the load bore by the active elements (e.g., drive winding, sense elements). A sensor with redundant drive windings and/or redundant sense elements is disclosed. The redundant elements may be connected to separate electronics. Another aspect relates to providing a reference transformer for calibration of a sensor. The secondary windings of the reference transformer are connected in series with the sense elements of the sensor to be calibrated. Transimpedance measurements are made when the drive winding of the reference transformer is excited. The measurements are used to correct transimpedance measurements made when the drive winding of the sensor is excited. A system having an impedance analyzer and a plurality of multiplexing units is disclosed for monitoring a plurality of sensor. Each multiplexing units directs an excitation signal to the drive winding of a respective sensor and returns, serially, the sense element responses back to the impedance analyzer. The system coordinates the excitation of each sensor and return of the sensor response to share a serial network. The multiplexing units may have a reference transformer for calibration of their respective sensors. Optical communication may be used.

15 Claims, 16 Drawing Sheets

DURABILITY ENHANCED AND REDUNDANT EMBEDDED SENSORS

This application claims the benefit of U.S. Provisional Application No. 61/303,033, filed on Feb. 10, 2010, which is herein incorporated by reference in its entirety.

The U.S. Government has a paid-up license in this invention and the right in limited circumstances to require the patent owner to license others on reasonable terms as provided for by the terms of contract number FA8501-09-P-0123 awarded by the Air Force.

BACKGROUND

Delayed detection of cracks in a component adds considerably to the cost of repair of products in the aerospace and other industries. Under some circumstances early detection of a crack may enables not only avoidance of catastrophic failure but also the ability to repair the component, thus increasing the life of the component and delaying the component's replacement.

Cracks are likely to form around high stress areas of a component such as near or at fastener holes. If a crack near a fastener hole is detected early, the hole may be oversized to eliminate the crack and extend the life of the component.

Conventional non-destructive testing (NDT) techniques for inspection at fastener holes have had difficulty detecting cracks early enough so that repair is possible. Accordingly the component may have to be replaced at considerable expense. Ultrasonic testing (UT) which detects reflections of a sound wave from within the component under test have proven to have difficulty detecting cracks beyond the first layer of a component, particularly when the sealant is not uniform or geometric variations reduce the probability of detection (POD) significantly below 1.0.

Conventional eddy current sensing involves the excitation of a conducting winding (the primary) with an electric current source of prescribed frequency. The current in the conducting winding produces a time varying magnetic field at the same frequency. By Faraday's law of induction an electromotive force is induced in a sensing winding (the secondary). The electromotive force may then be measured as a voltage. The spatial distribution of the magnetic field which is measured by the secondary is influenced by the proximity and physical properties (e.g., conductivity and permeability) of nearby materials. When the sensor is intentionally placed in close proximity to a test material, the physical properties of the material can sometimes be deduced from measurements of the transimpedance between the primary and secondary windings. Traditionally, scanning of eddy current sensors across the material surface is then used to detect flaws, such as cracks. Conventional eddy current testing (ET) has proven inadequate for detection of cracks near fastener holes in multiple layered structures. This is due to difficulty penetrating through thick outer layers and due to noise caused by geometric variations, fastener fit, and crack morphology variations.

SUMMARY

A substantially planar eddy-current sensor is disclosed that has durability enhancing pillars in an active region. The pillars are distributed and sized so as to have limited effect on the sensor's performance. When the sensor is mounted on a component such that the sensor experiences forces on a top and bottom surface, the pillars bear the load reducing the load bore by the active elements (e.g., drive winding, sense elements). A sensor with redundant drive windings and/or redundant sense elements is disclosed. The redundant elements may be connected to separate electronics.

Another aspect relates to providing a reference transformer for calibration of a sensor. The secondary windings of the reference transformer are connected in series with the sense elements of the sensor to be calibrated. Transimpedance measurements are made when the drive winding of the reference transformer is excited. The measurements are used to correct transimpedance measurements made when the drive winding of the sensor is excited.

A system having an impedance analyzer and a plurality of multiplexing units is disclosed for monitoring a plurality of sensor. Each multiplexing units directs an excitation signal to the drive winding of a respective sensor and returns, serially, the sense element responses back to the impedance analyzer. The system coordinates the excitation of each sensor and return of the sensor response to share a serial network. The multiplexing units may have a reference transformer for calibration of their respective sensors. Optical communication may be used.

Some aspects relate to a substantially planar sensor having a first surface and a second surface. The sensor comprises a drive winding, a sense winding, a plurality of pillars and a substrate. The drive winding is configured to guide an electrical current. The sense element configured to couple to a magnetic field produced if the drive winding is excited with the electric current. The plurality of pillars configured to protect the drive winding and sense element if the first and second surfaces are under load. The substrate configured to provide mechanical support to the drive winding, the sense element and the pillars.

In some embodiments the drive winding has a first dimension in a direction perpendicular to the first surface of the sensor; the sense element has a second dimension in the direction perpendicular to the first surface of the sensor, and each of the plurality of pillars has a third dimension in the direction perpendicular to the first surface of the sensor, said third dimension being greater than the first dimension and greater than the second dimension.

In some embodiments, the drive winding comprises a single turn.

In some embodiments, the sensor further comprises a redundant drive winding. The substrate may be formed from a plurality of layers and the drive winding and the redundant drive winding are formed between different layers of the substrate.

Some aspects relate to a sensor where the sense element is among a plurality of sense elements that are each configured to couple to the magnetic field if the drive winding is excited with the electrical current.

Some aspects relate to a sensor where the drive winding comprises a substantially circular portion and the substrate has a hole in a region comprising the center of the substantially circular portion of the drive winding.

Some aspects relate to a sensor where the drive winding is a first drive winding and the sensor further comprises a second drive winding having a substantially circular portion of a different radius than the substantially circular portion of the first drive winding.

Another aspect relates to a method of using a sensor to detect damage near a fastener hole of a component. The method comprises mounting the sensor at the fastener hole location of the component; driving the sense winding to produce the electric current; monitoring a response of the sense element to the electric current; and determining a damage condition of the component from the response.

Some aspects relate to a eddy-current sensor having a substantially planar surface. The sensor comprises a drive winding, a sense element, a plurality of pillars and a substrate. The plurality of pillars each pillar comprising a plurality of pillar elements that are aligned in a direction perpendicular to the substantially planar surface. The substrate configured to provide mechanical support to the drive winding, the sense element and the plurality of pillars.

Another aspect relates to a substantially planar eddy current sensor having a first surface and a second surface. The sensor has a first drive winding, a second drive winding, a plurality of sense elements, and a substrate. The first drive winding configured to guide a first electrical current, the first drive winding comprising a substantially circular portion having a first radius. The second drive winding configured to guide a second electrical current, the second drive winding comprising a substantially circular portion having a second radius greater than the first radius. The plurality of sense elements arranged about a perimeter of the substantially circular portion of the first drive winding, each sense element configured to couple to at least one of a magnetic field produced by the first electric current and a magnetic field produced by the second electric current. The substrate material configured to provide mechanical support to the first drive winding, the second drive winding and the plurality of sense elements.

In some embodiments, the sensor further comprises a plurality of pillars configured to protect the drive winding and sense element if the first and second surfaces are under load. The first drive winding may comprises a single, substantially circular portion having a first radius and wherein the sensor further comprises a substantially circular hole concentric with the substantially circular portion of the first drive winding, the hole having a second radius less than the first radius.

Some aspects relate to a sensor where the plurality of sense elements are arranged outside the perimeter of the substantially circular portion of the first drive winding and the second drive winding is so positioned such that the plurality of sense elements are arranged inside a perimeter of the substantially circular portion of the second drive winding. The first drive winding and the second drive winding may be connected in series.

Some aspects relate to a sensor where the plurality of sense elements are arranged outside the perimeter of the substantially circular portion of the first drive winding and the second drive winding is so positioned such that the plurality of sense elements are also arranged outside a perimeter of the substantially circular portion of the second drive winding.

Some aspects relate to a sensor where the substrate comprises a plurality of layers, the first drive winding is formed on a first layer surface and the second drive winding is formed on a second layer surface.

Some aspects relate to a sensor where the first layer surface and the second layer surface are opposite sides of a same layer among the plurality of layers of the substrate.

Some aspects relate to a sensor where the plurality of sense elements comprises a first subset of sense elements formed on the first layer surface, and a second subset of sense elements formed on the second layer surface.

Another aspect relates to a system for calibrating an eddy-current sensor. The system comprises a reference transformer, a source, and impedance analyzer and a processor. The reference transformer having a primary winding, a reference winding and a secondary winding, wherein the secondary winding is configured to be connected in series with a sense element of the eddy-current sensor. The source for providing a drive signal to the primary winding. The impedance analyzer configured to measure a first transimpedance of the series connected secondary winding and the sense element while the primary winding is excited by the source, and further configured to measure a second transimpedance of the series connected secondary winding and sense element while a drive winding of the sensor is excited. The processor configured to compute a calibrated transimpedance measurement using the first transimpedance and the second impedance.

Yet another aspect relates to a sensor monitoring system comprising a plurality of eddy-current sensors, an impedance analyzer and a plurality of multiplexing units. The plurality of eddy-current sensors, each sensor having a drive winding and a plurality of sense elements. The impedance analyzer configured to generate a control signal and an excitation waveform, and to measure a response waveform. The plurality of multiplexing units that are each connected in series with one another and the impedance analyzer and are each connected to a respective sensor among the plurality of sensors, each of the plurality of multiplexing units configured to provide the excitation waveform to the drive winding of the respective sensor in response to a trigger in the control signal and to sequentially pass each of the plurality of sense element responses to the impedance analyzer.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
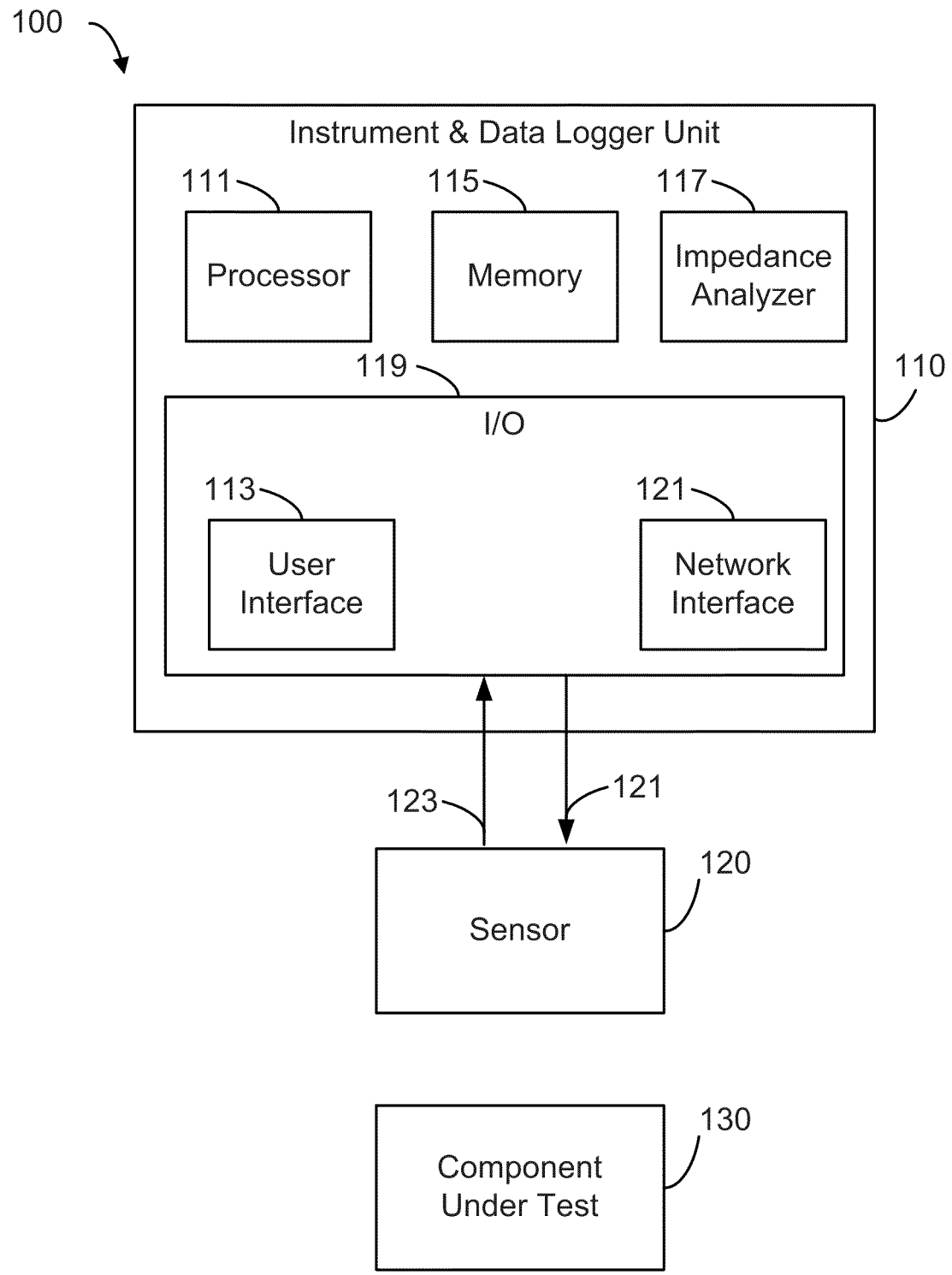
FIG. 1A is a system for inspecting a component under test according to some embodiments.

The inventors have recognized and appreciated that an improved sensing technology is needed to provide reliable detection of defects near fastener holes of a component. The sensor may be permanently mounted near the fastener hole to provide NDT measurements for the detection of defects near the fastener hole. In some embodiments, the sensor is substantially planar and is pressed to the component by the fastener, washer, or another component.

The inventors have recognized and appreciated that a sensor in this configuration may be subject to fretting and other forms of damage. Sensors are disclosed that include durability enhancing pillars which extend to provide load bearing support for the sensor. The pillars reduce the load burden on the drive winding and sense elements which increases the average life expectancy of the sensor. In some embodiments, the sensors are constructed of multiple substrate layers upon which drive windings, sensing elements (also referred to as sensing windings), pillar elements and the like are formed. Pillars may be formed by providing pillar elements at the same location in multiple layers such that a pillar is formed from the stack of pillar elements. This configuration allows the pillars to carry mechanical load, reducing the mechanical load carried by the active elements of the sensor (e.g., the drive windings, sense elements, and flux cancellation leads). Sufficient cumulative pillar area may be achieved by included numerous pillars over the sensor topology to provide sufficient surface area to carry the majority of the mechanical load seen by the sensor. The number of pillars, their shape and position may be selected to have a low interference with the functioning of the sensor while meeting other design requirements such as providing sufficient load bearing capacity.

The sensor may be provided with one or more redundant drive windings or one or more redundant sense elements (collectively "redundant elements"). The redundant elements are configured within the sensor topology to extend the life expectancy of the sensor. In some embodiments, the redundant elements are formed on a different surface or substrate layer than the winding or element which the redundant element duplicates. Each redundant drive winding or sense element may be laterally offset with respect to the winding or element which it duplicates such that when the sensor is under load the load is bore primarily by the pillars and not the windings. Furthermore, offsetting of redundant drive windings radially from the whole enables the outer winding to survive even if the inner winding fails. Each redundant drive winding and sense element may be connected to separate electronics such that the redundant elements may be measured independently of the elements they duplicate. In some embodiments, a multiplexer is used to separately measure each sense element response. In one such embodiment, at least two multiplexing units are included to record data from independent, redundant sensors.

The sensor may be excited and the response measured using an instrument having an impedance analyzer. In some embodiments the impedance analyzer may use a reference transformer to recalibrate the sensor. Recalibration may be used to correct for contributions to the measurement that are due to the measurement system and not the component under test. For example, drift of the system due to temperature variation may be corrected for using a reference transformer.

Under many practical scenarios, several embedded or mounted sensors may be monitored by the same instrumentation. Conventionally a parallel architecture has been used to connect these sensors to the impedance instrument. The inventors have recognized that in many of these sensor applications data rate is not a critical factor as the sensors are stationary (not scanning) and the material properties are changing only slowly over time. A serial topology for monitoring the sensors is provided that drastically reduces the cost and setup time associated with such a network of sensors. The measurement instrumentation is connected to a set of series connected multiplexing units. Each multiplexing unit has a respective sensor attached thereto. The instrument may provide an excitation signal and control signals. The multiplexing units take turns in accordance with the control signal providing the excitation signal to their respective sensor's drive winding and returning the sense element response to the instrument for characterization. If the sensor has multiple sense elements, the multiplexing unit may sequence the return of each sense element response to the instrument for measurement. In another embodiment, the impedance measurement electronics may be miniaturized and located locally at each sensor location (node). In one such embodiment the impedance response is converted to an optical signal and transmitted optically. In this configuration higher data acquisition rates can be provided to support such applications such as torque and load monitoring.

Having discussed some embodiments generally, attention is now turned to the drawings. FIG. 1A is a block diagram of a system 100 for monitoring the condition of a component under test 130. System 100 includes an instrument and data logger unit 110 (instrument 110) and a sensor 120. Instrument 110 is configured to provide excitation signals 121 to sensor 120 and measure the resulting response signals 123 of sensor 120. Sensor 120 may be positioned proximal to (e.g., by mounting) or embedded within a component under test 130 such that response signals 123 may be processed to estimate properties of component 130.

Instrument 110 may include a processor 111, a user interface 113, memory 115, an impedance analyzer 117, an input/output (I/O) unit 119, and a network interface 121. While instrument 110 is drawn as a single block, it should be appreciated that instrument 110 may be realized as a single "box"; multiple, operably-connected "boxes", or in any other suitable way. For example, in some embodiments it may be desired to provide certain components of instrument 110 as proximal to sensor 120 as practical, while other components of instrument 110 may be located at greater distance from sensor 120. Though, the configuration of the components of instrument 110 with respect to sensor 120 and component 130 is not critical to the invention and any suitable configuration may be used.

Processor 111 may be configured to control instrument 110 and may be operatively connected to memory 115. Processor 111 may be any suitable processing device such as for example and not limitation, a central processing unit (CPU), digital signal processor (DSP), controller, addressable controller, general or special purpose microprocessor, microcontroller, addressable microprocessor, programmable processor, programmable controller, dedicated processor, dedicated controller, or any suitable processing device. In some embodiments, processor 111 comprises one or more processors, for example, processor 111 may have multiple cores and/or be comprised of multiple microchips.

Memory 115 may be integrated into processor 111 and/or may include "off-chip" memory that may be accessible to processor 111, for example, via a memory bus (not shown). Memory 115 may store software modules that when executed by processor 111 perform a desired functions. Memory 115 may be any suitable type of computer-readable storage medium such as, for example and not limitation, RAM, a nanotechnology-based memory, one or more floppy disks, compact disks, optical disks, volatile and non-volatile memory devices, magnetic tapes, flash memories, hard disk drive, circuit configurations in Field Programmable Gate Arrays (FPGA), or other semiconductor devices, or other tangible, non-transient computer storage medium.

Instrument 110 provides excitation signals for sensor 120 and measures the response signal from sensor 120 using impedance analyzer 117. The sensor transimpedance may be measured using one or more excitation signals at on one or more sense elements of sensor 120. In some embodiments, time harmonic sinusoidal signals of a prescribed frequency may be used to excite the drive winding of sensor 120. Though any suitable excitation signal may be used. Instrument 110 may process the transimpedance data to estimate one or more properties of component under test 130. Methods and apparatus for processing transimpedance data to estimate material properties are disclosed, for example, in U.S. Pat. Nos. 7,696,748 and 7,467,057 which are hereby incorporated by reference in their entirety.

Memory 115 of instrument 110 may store computer executable software modules that contain computer executable instructions. These modules may be read for execution by processor 111. Though, this is just an illustrative embodiment and other storage locations and execution means are possible. In some embodiments, aspects of impedance analyzer 117 may be implemented as computer executable modules. Though, impedance analyzer 117 may be implemented using any suitable combination of hardware and/or software.

Instrument 110 may include an input/output (I/O) unit 119. I/O 119 comprises any suitable hardware and software for interfacing with instrument 110. For example, I/O 119 may include a user interface 113 and a network interface 121. I/O 119 may also comprise components for interfacing with sensor 120.

User interface 113 may include devices for interacting with a user. These devices may include, by way of example and not limitation, keypad, pointing device, camera, display, audio input and audio output.

Network interface 121 may be any suitable combination of hardware and software configured to communicate over a network. For example, network interface 121 may be implemented as a network interface driver and a network interface card (NIC). The network interface driver may be configured to receive instructions from other components of instrument 110 to perform operations with the NIC. The NIC provides a wired and/or wireless connection to the network. Wired connections may use metal wires, optical fibers with appropriate interface electronics, or any other suitable wired connection technology or combinations of technologies. Networks may be in a loop with sensor modes hung off said loop, or with individual direct connections to a central data acquisition unit. The NIC is configured to generate and receive signals for communication over the network. In some embodiments, instrument 110 is distributed among a plurality of networked computing devices. Each computing device may have a network interface for communicating with other computing devices forming instrument 110.

As discussed above instrument 110 may be operably connected to sensor 120 through I/O 119. Sensor 120 may be any suitable type of sensing technology, for example, an eddy-current sensor. Sensor 120 may include one or more drive windings and one or more sense element. If sensor 120 has more than one drive winding the windings may be redundant and/or provide different spatial modes of the magnetic field for interrogation of component 130.

Figure 1B:
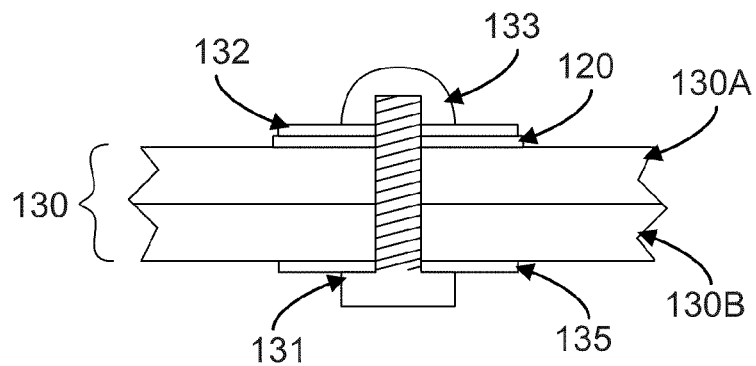
FIG. 1B is a cross section of the component under test and a sensor adapted for inspection near a fastener hole according to some embodiments.

FIG. 1B illustrates how sensor 120 may be adapted to inspect component under test 130. In the illustrated embodiment, component 130 comprises materials 130A and 130B that are held together by a fastening hardware. As illustrated, the fastening hardware comprises a bolt 131 which passes through a fastener hole in materials 130 and 130B, a nut 133 and washers 132 and 135. Sensor 120 may have a hole through which bolt 131 passes through. Sensor 120 may be pressed to component 130 by washer 132. To prevent shear loads from being transferred while securing the fastener, washer 132 may be prevented from rotating during mounting by using a tab, a dual washer configuration that anchors the washer from rotating using a second hole, or in any suitable way. In some embodiments sensor 120 may be mounted under washer 135 or sensors may be mounted under both washer 132 and 135. It should be appreciated that other configurations are possible and the illustration of mounting sensor 120 as shown and described with connection to FIG. 1B is merely illustrative. Sensor 120 may be mounted, embedded or proximally placed to component 130 in any suitable way.

Figure 2A:
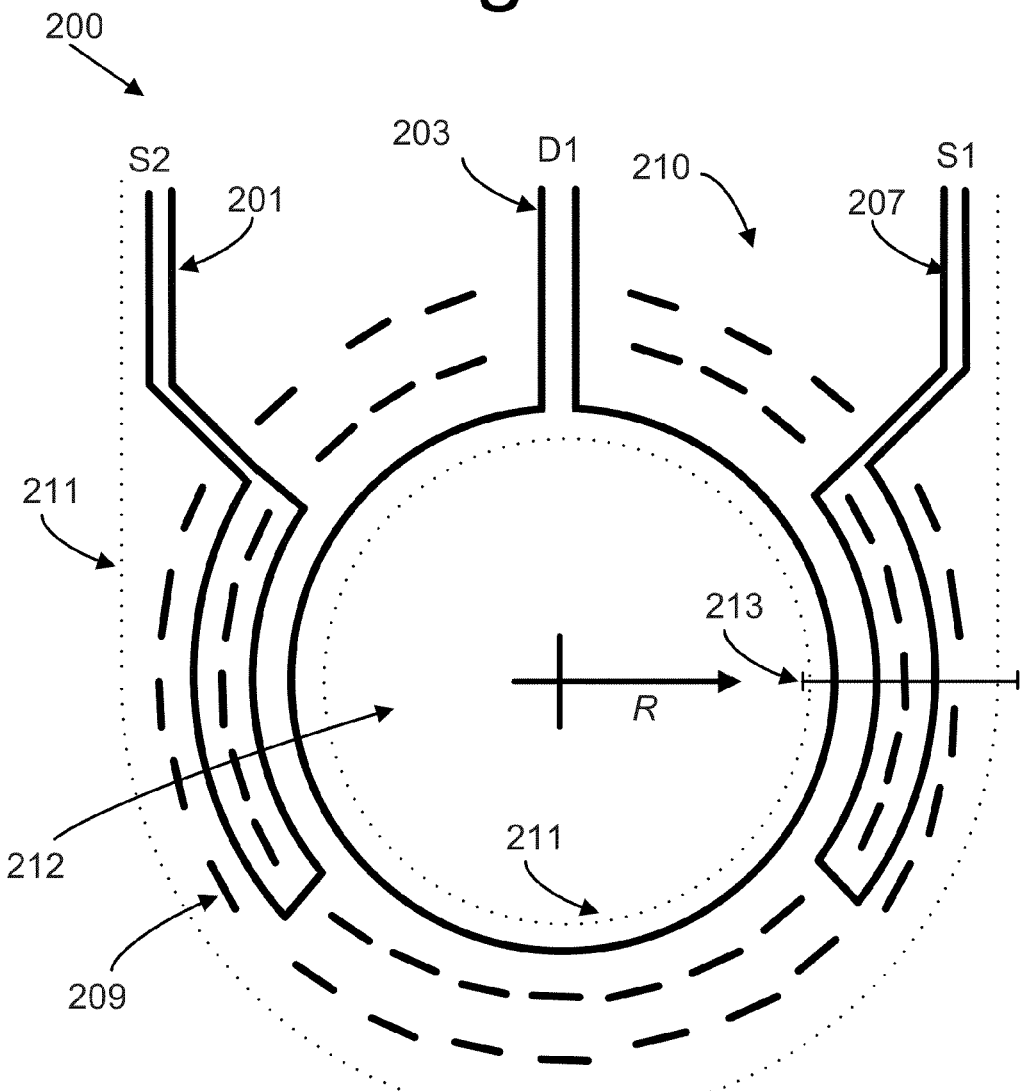
FIG. 2A is a depiction of the active area of a sensor having durability enhancing pillars according to some embodiments.

Aspects of some embodiments of sensor 120 are now discussed with reference to FIGS. 2A-7B. FIG. 2A shows the active area of a sensor 200 according to some embodiments. Sensor 200 may be used as an embodiment of sensor 120 in FIG. 1A and may be configured to inspect a component under test as shown in FIG. 1B. Though, sensor 200 may be used in any suitable configuration. As shown in FIG. 2A, sensor 200 includes a drive winding 203, a first sense element 207 and a second sense element 201. Drive winding 203 and sense elements 201 and 207 may be formed from highly conducting materials such a metal or metal alloy (e.g., electroplated copper). Drive winding 203 and sense elements 201 and 207 may extend to a connector (not shown) for interfacing sensor 200 with an instrument (e.g., instrument 110, FIG. 1A). Though, any suitable connection may be used for interfacing with sensor 200.

Sensor 200 is also provided with a plurality of durability enhancing pillars 209. Pillars 209 may be made of any suitable material that provides rigidity to sensor 200 in the vertical direction (into and out of the page) and to substantially bear a load placed on sensor 200 when mounted for measurement of a component under test. This relieves the drive and sense elements from bearing this load and reduces the likelihood that these active elements will be damaged. In some embodiments, durability enhancing pillars 209 are formed of the same material as drive winding 203 and sense elements 201 and 207. For example, pillars 209 may be formed from pillar elements etched from electroplated copper in the same manufacturing step in which drive winding 203 and sense elements 201 and 207 are formed. Pillars may be arranged in patterns around drive winding 203 and sense elements 201 and 207. Design considerations in the size and density of the pillars include, the amount of force the mounted sensor will experience, the life requirements for the sensor, the extent to which the presence of the pillars will be modeled in interpreting the sensor response, and the sensitivity to flaws required of the sensor.

Drive winding 203, sense elements 201 and 207 and pillars 209 may be formed on and/or embedded within a low-conductivity substrate 210 that maintains the substantially planar sensor geometry. The boundary of the substrate is demarcated by dotted line 211. Flexible substrate materials may be used so that the sensor may be conformed to a flat or curved surface. Though, more rigid materials may be used for a planar configuration of the sensor or for a curved configuration of the sensor. In some embodiments, substrate 210 is provided by one or more layers of poly(4,4'-oxydiphenylene-pyromellitimide) ("Kapton" available from E. I. du Pont de Nemours and Company). Multiple layers may be held together by a suitable adhesive. The active elements may be embedded between the layers. Though, any suitable substrate material and configuration may be used.

Sensor 200 may be provided with a hole 212 in substrate 210 through which a fastener may pass. Sensor 200 may be mounted such that the fastener presses sensor 200 against the component under test. Sensor 200 may then be used for detection of flaws near the fastener hole of the component under test. Drive winding 203 is shown having as substantially circular portion around hole 212 such that a current may be provided around the fastener hole of the component and produce a magnetic field within the component proximate to the fastener hole. Sense elements 201 and 207 may be positioned to couple to the magnetic field passing through areas of the component under test that are disposed to developing flaws (e.g., cracks). Such areas may be identified a priori, for example, by simulating the stresses on the component under test via software of fatigue tests, by analysis of failed components, or in any suitable way. It should be appreciated that while the fastener hole shown in FIG. 2A is circular as are the drive 203 and surrounding sense elements 201 and 207, and suitable drive winding and sense element shape may be used. A suitable geometry may be dictated by the specific application for which sensor 200 is being used.

Figure 2B:
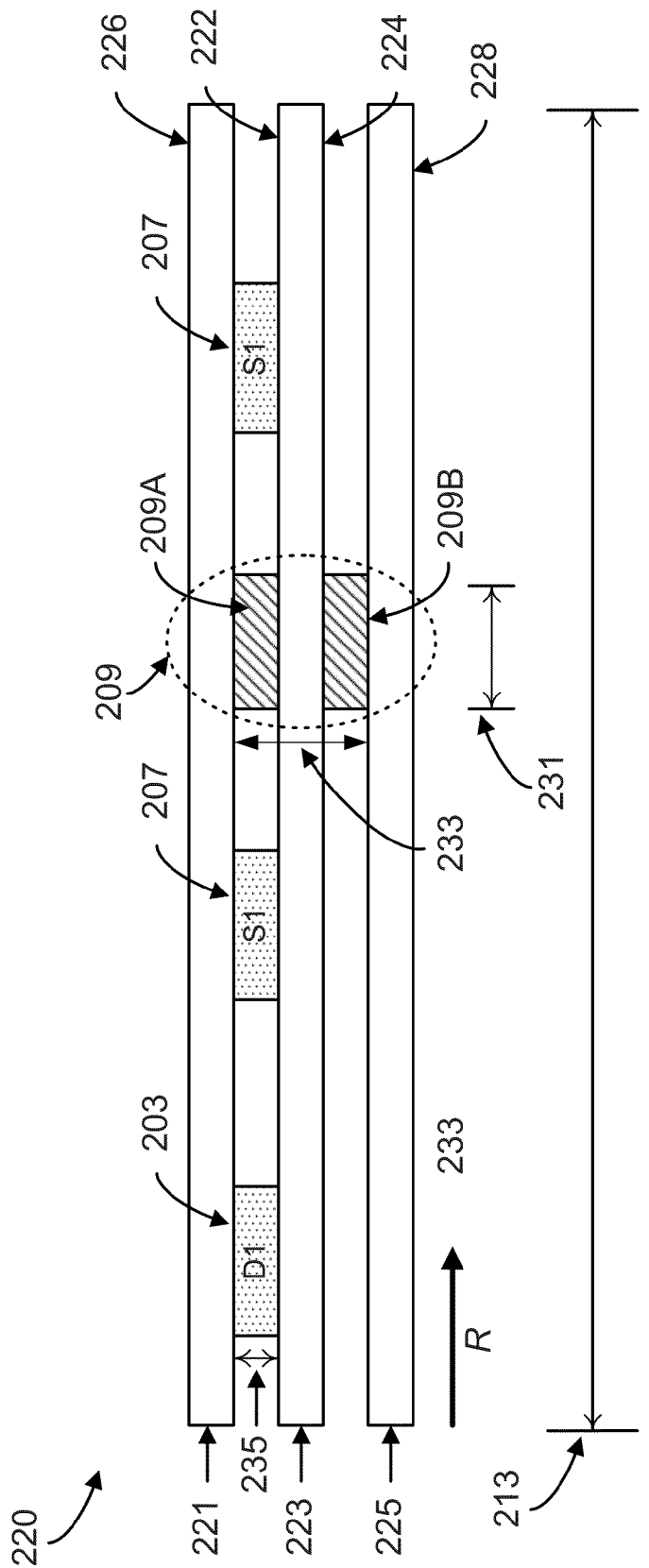
FIG. 2B is a cross section of a sensor having durability enhancing pillars according to some embodiments.

Reference line 213 of FIG. 2A indicates the location of a cross-section 220 of sensor 200 shown in FIG. 2B. In the embodiment illustrated in FIG. 2B, sensor 200 comprises substrate layers 221, 223, and 225. Drive winding 203, sense winding 207 and pillar 209 may be formed, for example, by electroplated copper on the surface of one or more substrate layers. The electroplated copper may be etched to form the specific drive winding, sense elements and pillars required by a particular sensor design. For example, substrate layer 223 may have electroplated copper on both side 222 and 224. Drive winding 203, sense element 207 and pillar element 209A may be etched on surface 222 and pillar element 209B may be etched on surface 224. Note that pillar 209, which is formed by pillar elements 209A and 209B, has a vertical dimension 233 that is greater than the vertical dimension 235 the drive and sense windings. Substrate layers 221 and 225 may be provided to provide further protection for the drive winding and sense elements.

In this embodiment the strength of the pillar is enhanced by vertical aligning (i.e., in a direction perpendicular to the sensors surface 226) pillar elements 209A and 209B. The lateral dimension 231 of the pillar elements 209A and 209B may be chosen with consideration to the accuracy of alignment that can be achieved between these element in the manufacturing process. It should be appreciated that the lateral dimension 231 of pillar elements 209A and 209B may be the same or different. Similarly, the vertical dimension of the pillar elements 209A and 209B may be different. For example, surfaces 222 and 224 may be electroplated with different weights of copper. While pillar 209 is shown to be formed from two pillar elements, more or less elements may be used provided the pillar is able to reduce the load experienced by the drive winding and sense elements if a load is applied to surfaces 226 and 228 of sensor 200.

A suitable adhesive (not shown for clarity) may be used between layers 221, 223 and 225 to hold the layers together with the proper alignment. The adhesive and substrate layers 221, 223, and 225 may provide less rigidity than the pillar elements 209A and 209B. Accordingly, when the sensor is mounted on a component for test and receives a force upon surfaces 226 and 228 the adhesive and substrate layers may compress while the pillar elements substantially bear the load. While specific manufacturing processes used for sensors according to some embodiments have been referred to with reference to FIG. 2B, it should be appreciated that the process used to form sensor 200 is not critical to the invention and any suitable manufacturing process may be used.

Figure 3A:
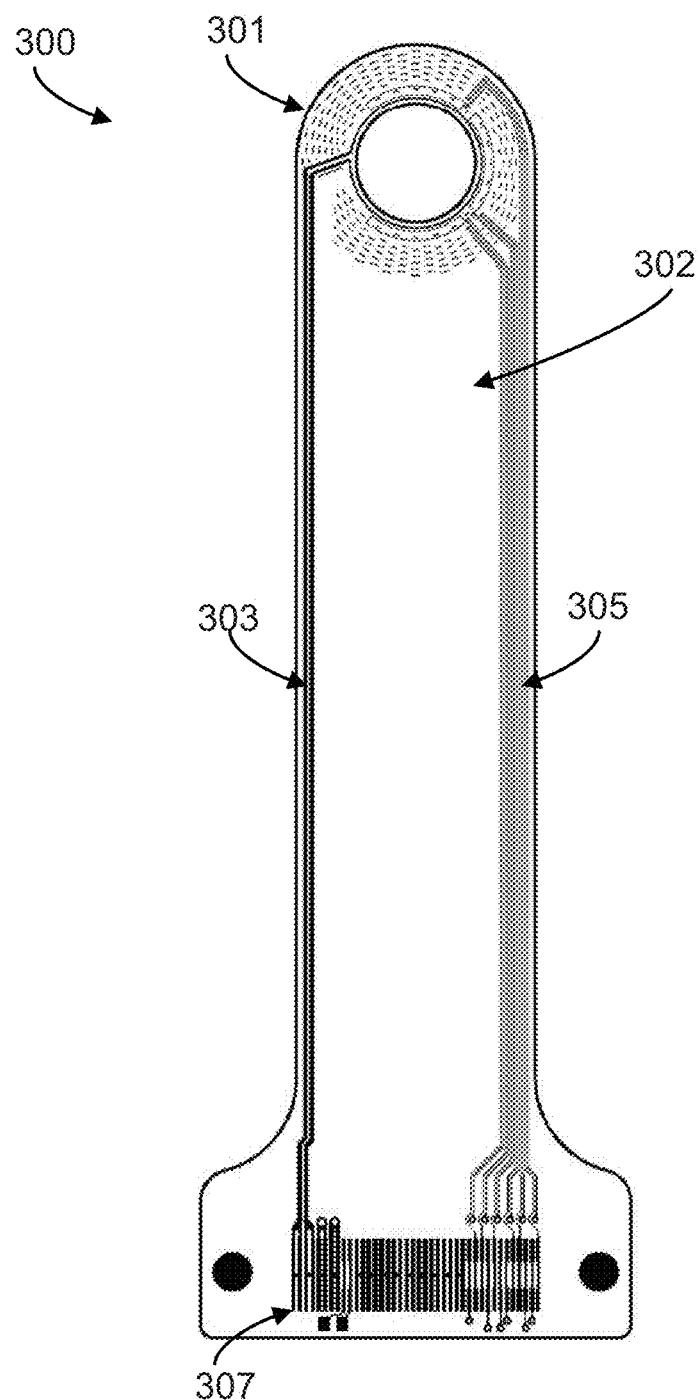
FIG. 3A is a schematic of a sensor having durability enhancing pillars adapted for inspection near a fastener hole according to some embodiments.

Turning now to FIG. 3A, a sensor 300 is shown. Sensor 300 may be used as an embodiment of sensor 120 in FIG. 1A. Though, sensor 200 may be used in any suitable configuration. Sensor 300 includes a active area 301, a substrate 302, drive leads 303, sense leads 305, and a connector area 307. The length of drive leads 303 and sense leads 307 may be determined by the particular application or any suitable way. Any suitable connector 307 may be used for interfacing with sensor 300.

Figure 3B:
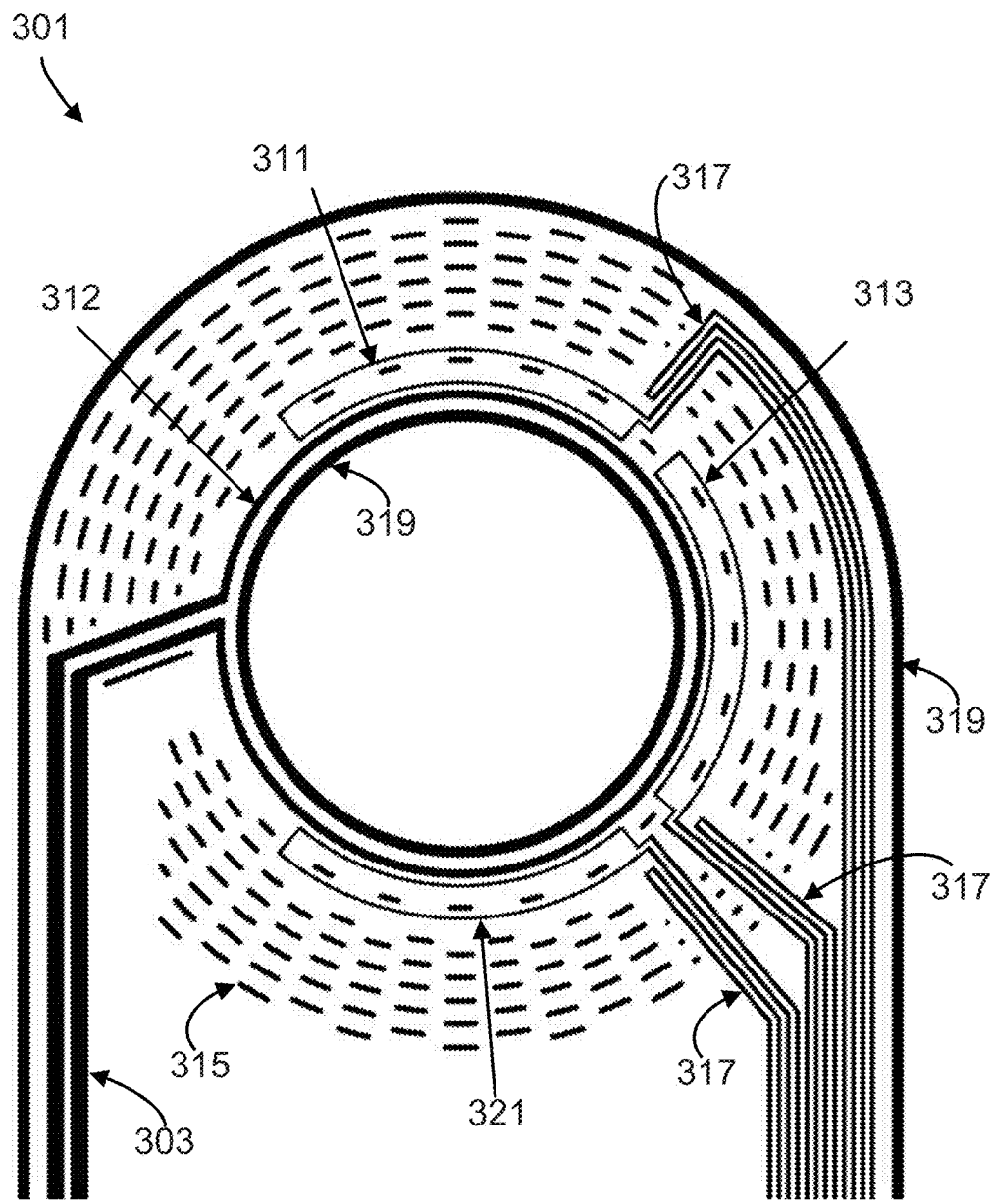
FIG. 3B is a detailed drawing of the active area of the sensor adapted for inspection near a fastener hole having durability enhancing pillars according to some embodiments.

Turning now to FIG. 3B, a detail of the active area 301 is shown. The active area includes a drive winding 312 which has a substantially circular loop consisting of one turn connected to drive leads 303. Active area 301 also includes three sense elements in the embodiment shown. Sense elements 311 and 303 are located at the "top" and "bottom" of the sensor's active area (relative to the drawing orientation). When sensor 300 is mounted, these sense elements may couple to a portion of the magnetic field generated by a current through drive winding 312 that passes through a region of the component under test where cracks or other flaws are expected to develop. Sense element 313 in turn may be positioned on the component under test at a location that is not likely to develop flaws. The response from sense element 313 may be used to provide a reference point that may be used for comparison for the responses measured on sense element 311 and sense element 321.

Sensor 300 may also include flux cancellation leads 317 for each of the sense elements 303, 311 and 313. Flux cancellation 317 follows the path of the associated sense element lead up to the point of the sense element area. Because of the proximity of the flux cancellation lead to the actual sense element leads, the flux through sense element lead can be approximated by the flux through the flux cancellation lead. Accordingly, the component of the sensed response attributed to the sensor leads can be corrected for (e.g., by instrument 110, FIG. 1A) such that the remaining sensed response may be attributed to contributions from the region of interest. The use and design of flux cancellation leads is detailed in U.S. Pat. Nos. 6,657,429 and 7,049,811 which are hereby incorporated by reference.

Figure 3C:
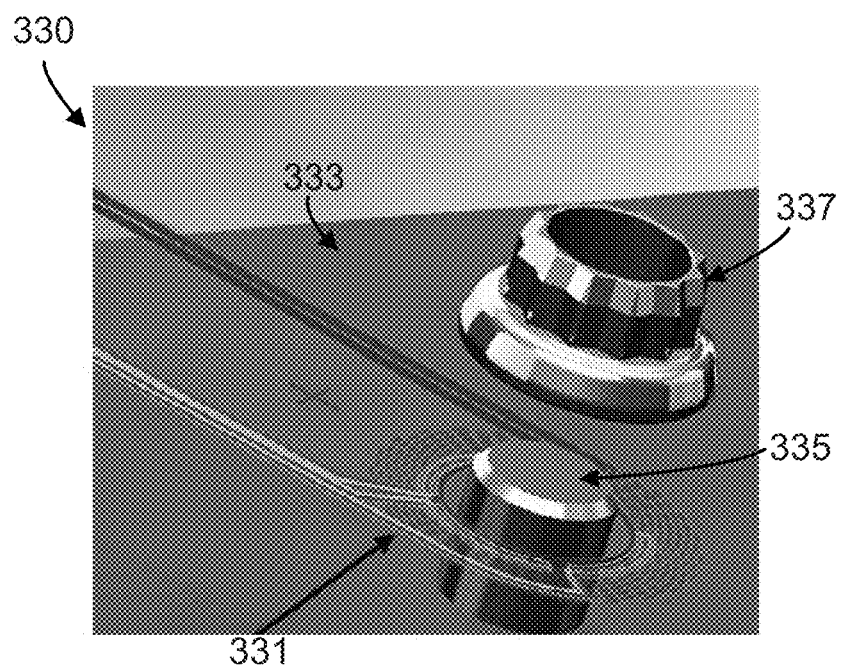
FIG. 3C is a rendering illustrating mounting of a fastener hole sensor at a fastener hole according to some embodiments.
Figure 3D:
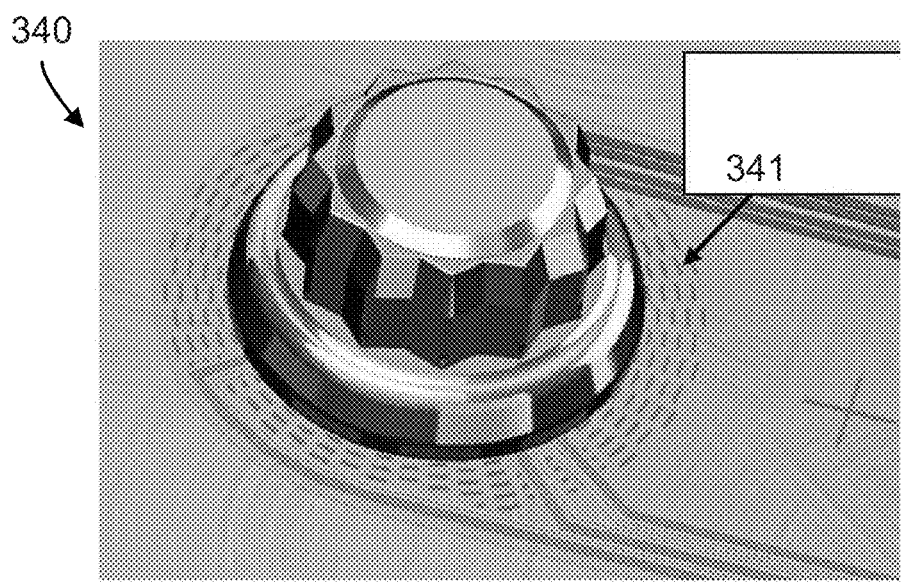
FIG. 3D shows a fastener hole sensor mounted at a fastener hold and held by a fastener according to some embodiments.

FIGS. 3C and 3D show rendered images 330 and 340, respectively, of how a sensor 331 may be mounted and used in a fastener application. As shown in rendering 330 a fastener bolt 335 is provided through a hole in component under test 333 and through a hole in sensor 331. A fastener cap 337 (e.g., a nut and washer) can then be applied and secured as shown in rendering 340 (FIG. 3D). The tightened fastener produces pressure against sensor 331 which is bore primarily by the pillars 341 of sensor 300. The pillars under the fastener cap will substantially bear the load on the sensor. The remaining pillars that are outside the radius of the fastener cap will not be substantially load bearing. Though, they provide the flexibility to use a larger surface area fastener cap. It should be appreciated that this is merely one illustrative use of a sensor with pillars; the invention is not so limited.

Figure 4A:
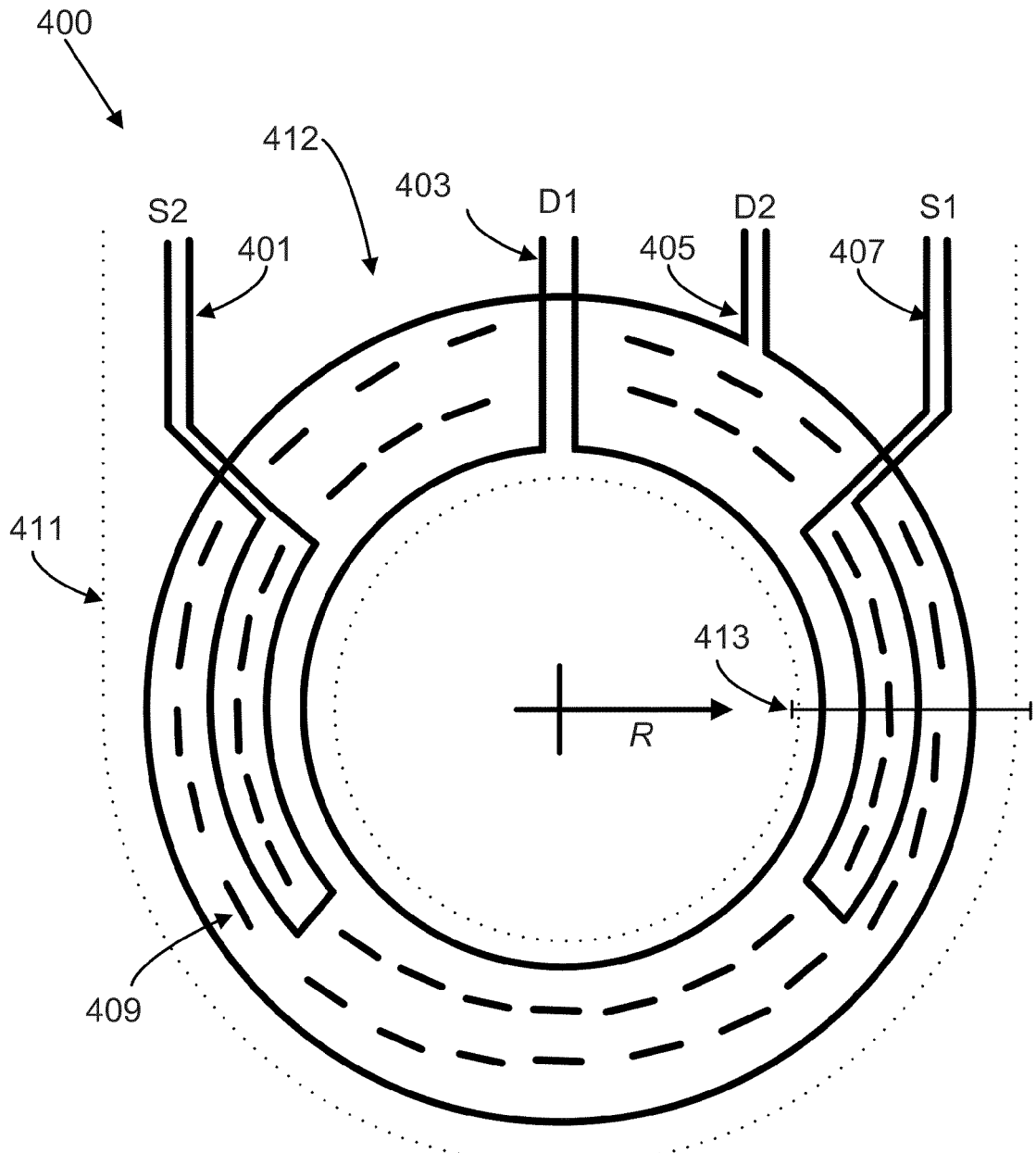
FIG. 4A is an illustration of the active area of a sensor having durability enhancing pillars and an inner and outer drive winding according to some embodiments.

FIG. 4A illustrates a sensor 400 with a "near" drive winding 403 and a "far" drive winding 405. Sensor 400 may be used as a specific embodiment of sensor 120 shown in FIG. 1. Though, sensor 200 may be used in any suitable configuration. Sensor 400 may include one or more sense elements such as sense elements 401 and 407. While drive winding 405 appears to cross drive winding 403 and sense elements 401 and 407 a short circuit is avoided because drive winding 405 is formed in a different plane than drive winding 403 or sense elements 401 and 407. Sensor 400 is also provided with pillars 409 in the active area of the sensor. Sensor 400 includes a substrate 412 with boundary 411. As for sensors 200 (FIG. 2A), 300 (FIGS. 3A-3B) and 331 (FIGS. 3C-3D) sensor 400 is illustrated with a hole in the center of the active area through which a fastener may pass if sensor 400 is to be mounted near a fastener hole of a component under test. As for the above sensors, this configuration is illustrative and sensor 400 may be adapted for any suitable application. The pillars 409 are provided in short contact points distributed around the sensors active area such that the sensor response is not substantially affected by the presence of the pillars 409 because the effect of pillar 409 is insubstantial on the sensor response, sensor 400 can be used to detect defects of interest in components under test. Drive winding 403 and drive winding 405 are positioned radially inside and outside, respectively, of both sense elements 401 and 407. This configuration permits magnetic fields be generated and monitored in different regions of the component under test. When sensor 400 is mounted near a fastener hole, for example, the inner drive winding 403 produces a magnetic field that penetrates a region of the component under test most proximal to the fastener hole. The outer drive winding 405 produces a magnetic field that penetrates a region of the component under test further away from the fastener hole, i.e., at larger radius. This configuration permits detection of cracks or other defects that originate near the fastener hole wall or further away from the fastener hole wall.

Figure 4B:
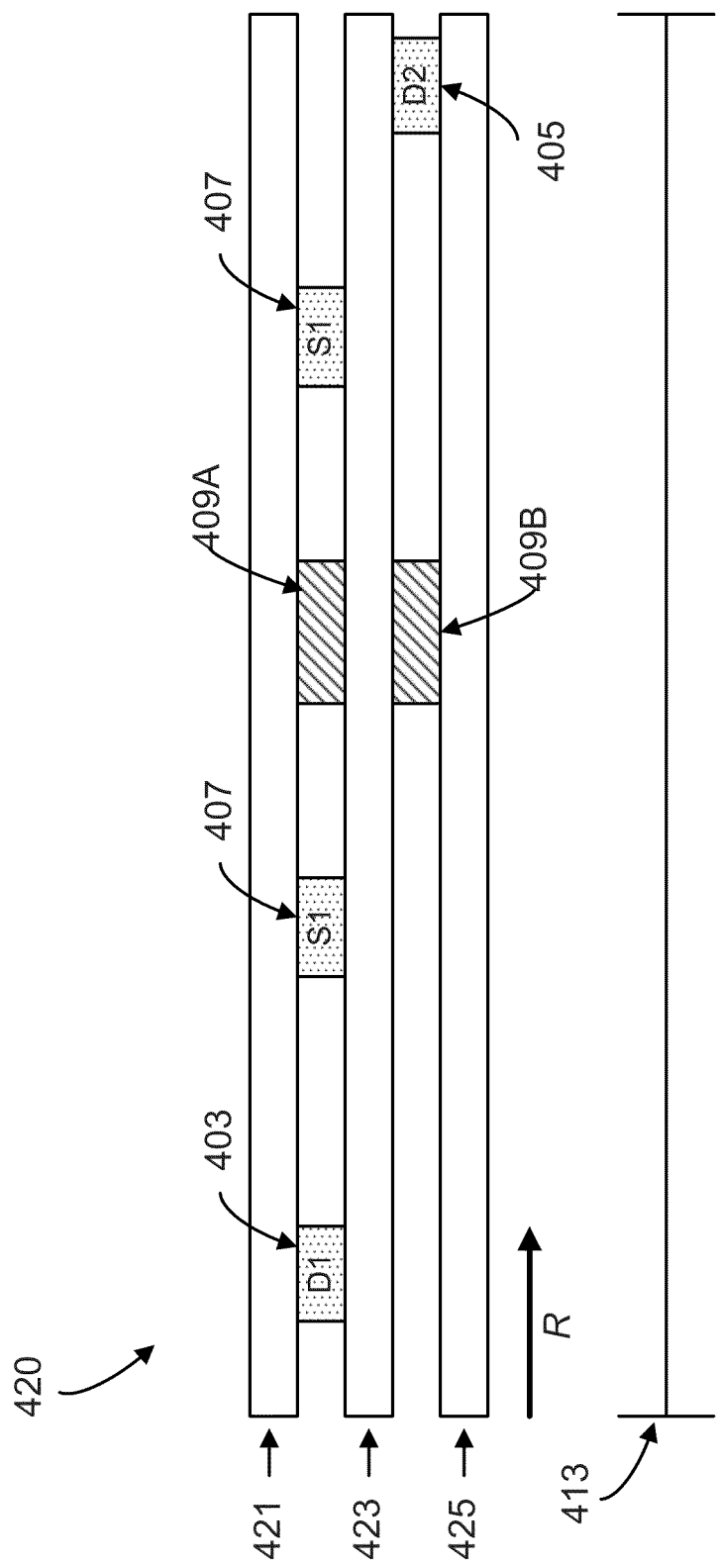
FIG. 4B is a cross section of a sensor having two drive windings and a durability enhancing pillars according to some embodiments.

Line 413 on FIG. 4A indicates the location of the cross-section 420 of sensor 400 shown in FIG. 4B. Cross-section 420 at line 413 illustrated in FIG. 4B is an embodiment of sensor 400 wherein the substrate is formed from substrate layers 421, 423 and 425 and from a joining adhesive therebetween. Sensor 400 may be manufactured in ways described with connection with FIG. 2B or in any suitable way. Cross-section 420 shown in FIG. 4B is identical to cross-section 220 of FIG. 2B except that cross-section 420 includes the addition of drive winding 405 which is printed in a different plane (here between substrate layers 423 and 425) than drive winding 403.

Figure 5:
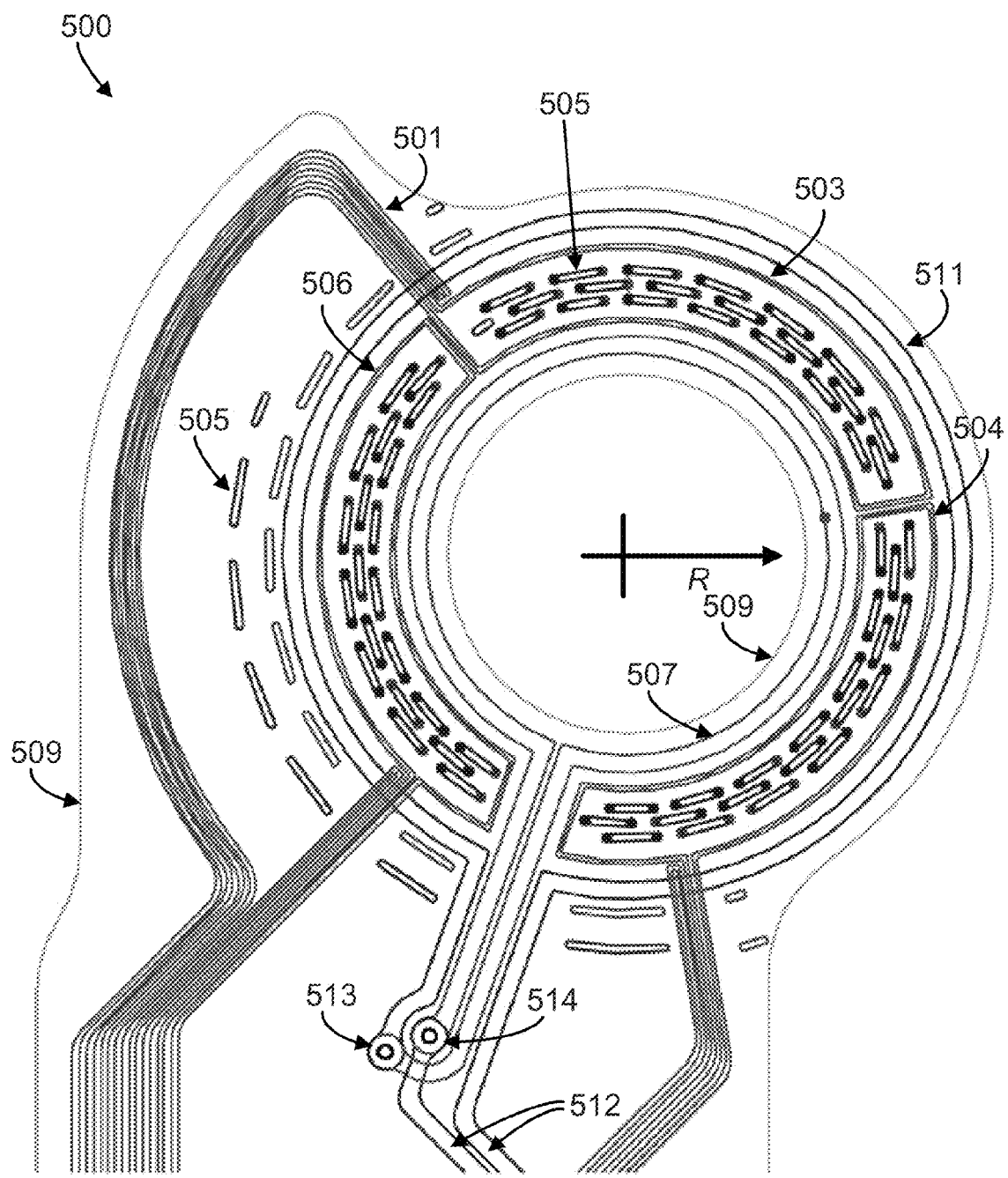
FIG. 5 shows a sensor having durability enhancing pillars and an inner and outer drive winding according to some embodiments.

FIG. 5 shows an embodiment 500 of yet another sensor, sensor 500. Note that in FIG. 5, the edges of each trace are drawn; the areas are not "filled in" as in the preceding sensor drawings. Sensor 500 includes an inner drive winding 507 and outer drive winding 511 connected in series such that the current on the inner drive winding is in the same direction circumferentially as the current on the outer drive winding 511. In order to achieve this configuration, a via 513 is provided to connect the inner winding 507 to outer winding 511. A second via 514 is provided to permit the drive winding leads 512 to be in the same plane. Inner drive winding 507 and outer drive winding 511 are printed in different layers of the substrate of sensor 500.

Sensor 500 also includes sense elements 503, 504 and 512. In the illustrated embodiment, sense elements 503 are printed in the same material layer as the inner drive winding 507, though any suitable configuration may be used. Each sense winding may have a flux cancellation lead such as flux cancellation lead 501 for sense element 503. Because the central drive winding and the outer drive winding have currents traveling in the same direction, it is possible to detect surface breaking and buried cracks with low to mid frequency eddy current signals.

Figures 6A, 6B:
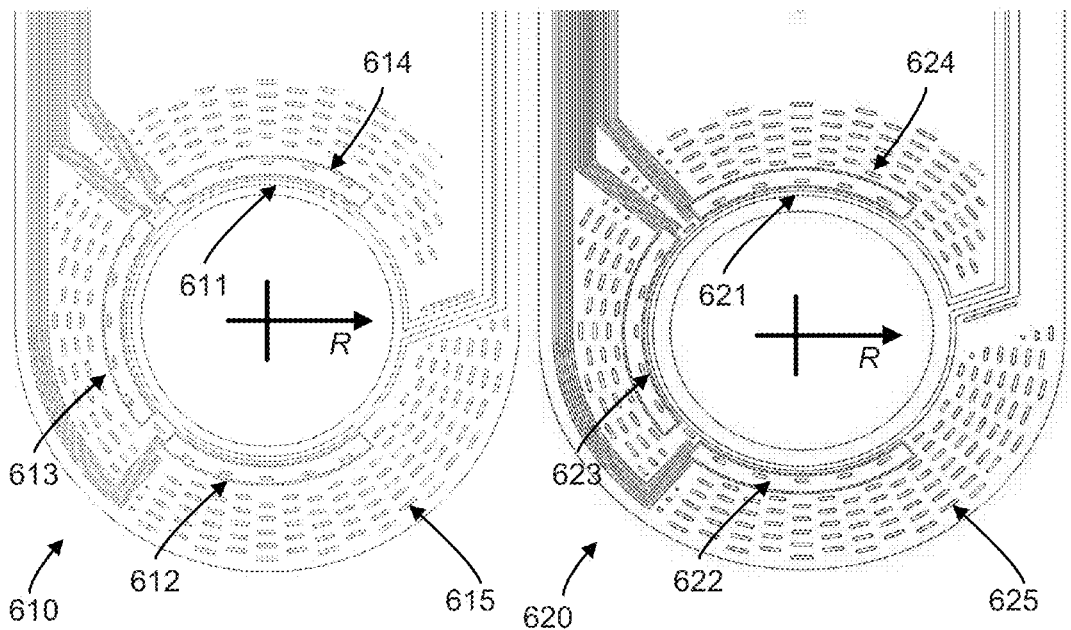
FIG. 6A-6C show a sensor having redundant drive and sense windings.
Figure 6C:
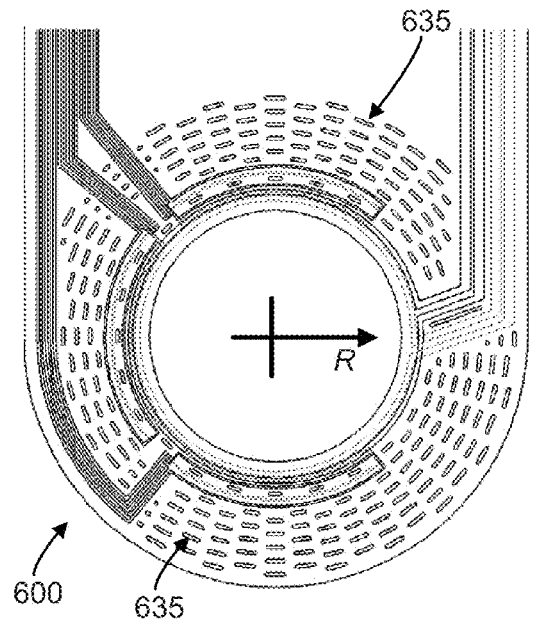

FIGS. 6A, 6B and 6C show portions of yet another sensor (sensor 600). Specifically, FIG. 6A shows a layer 610 of sensor 600 and FIG. 6B shows a layer 620. FIG. 6C shows the layer 610 and layer 620 superimposed upon one another to form sensor 600. That is FIG. 6C shows the layers 610 and 620 as they would be stacked on top of one another to form sensor 600. It can be seen in FIG. 6A that the layer 610 has a drive winding 611 three sense windings, 614, 613 and 612, and a plurality of pillar elements 615 which are distributed around the entire active area of layer 610. FIG. 6*b* shows layer 620 which has a drive winding 621, three sense winding 622, 623 and 624, and partial pillars 625 that are distributed around the entire active area of layer 620. A close comparison of layer 610 and layer 620 reveals that the drive winding 611 has a circular portion with a slightly smaller radius than the circular portion of drive winding 621. Similarly, the sense elements are formed as arcs at slightly different radii than the sense elements 622, 623, and 624 in FIG. 6B. The pillar elements 615 and 625, however, are aligned with one another such that they form pillars 635.

As the drive winding 621 produces a magnetic field that may be used to provide sensitivity to substantially the same defects as drive winding 611 these drive windings are said to form a redundant pair. If one drive winding fails (e.g., by a crack therein that prevents current from traveling), substantially the same magnetic fields may be produced in a component under test. Similarly, sense elements 612 and 622 for a redundant pair as do sense elements 613 and 623, and sense elements 614 and 624.

Because the redundant pairs are laterally offset from one another while pillars 635 are not the pressured applied to sensor 600 when used in an application is bore primarily by pillars 635 rather than the sense elements or drive windings. If during use however, a drive winding or sense elements fails, the redundant windings and sense elements provide assurance that the component under test can continue to be monitored.

Figure 6D:
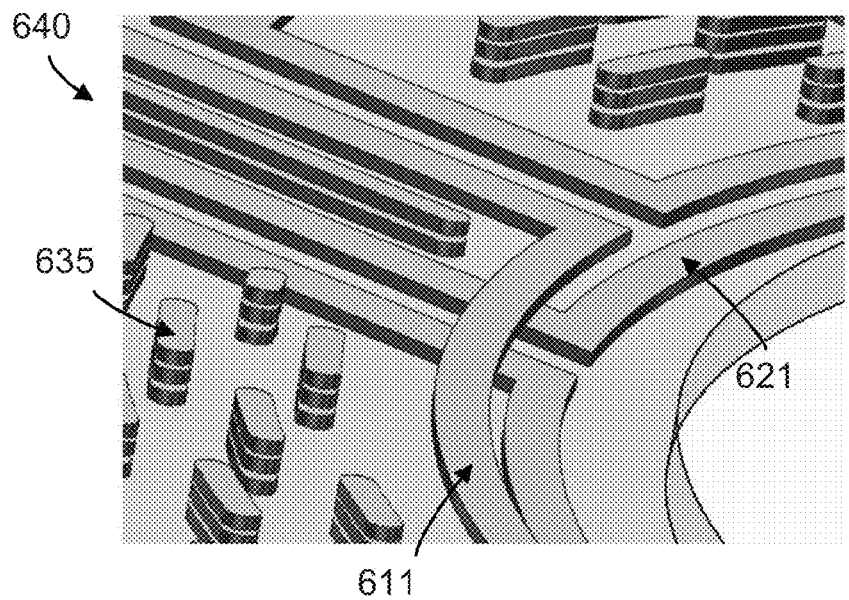
FIG. 6D shows a rendering of a sensor having redundant drive windings.

FIG. 6D shows a rendering 640 of the area of sensor 600 where the two drive windings are connected to the leads. It can be seen from rendering 640 that the drive windings may be formed in different layers and are of slightly different radii than one another.

Rendering 640 also illustrates a third layer not previously shown that includes only pillar elements. As illustrated in rendering 640 these pillar elements are formed as a layer between the layers of the first and second drive windings. Thus, the complete pillar is formed by the pillar elements in the layer with the first drive winding the pillar elements in the layer with the second drive winding and the pillar elements in an intermediate layer without any drive windings.

Figure 6E:
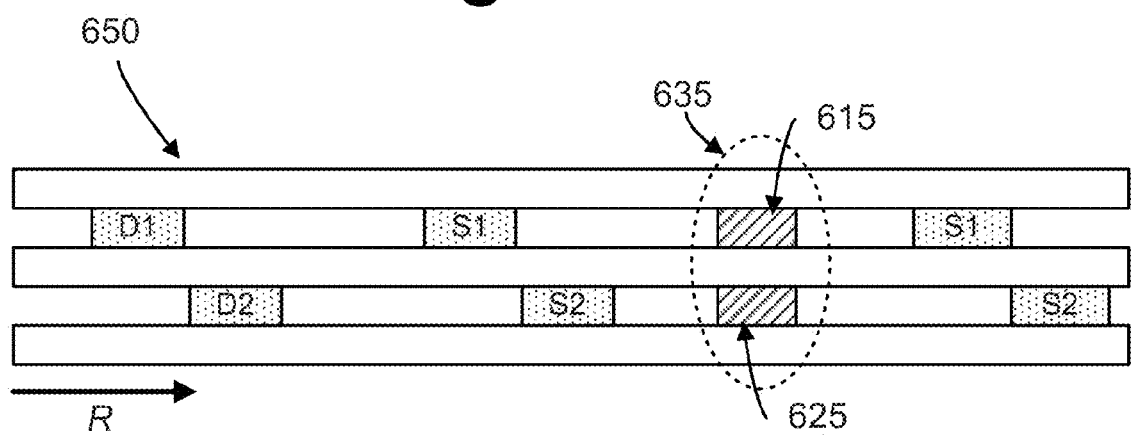
FIG. 6E shows a cross section of a sensor having durability enhancing pillars redundant drive winding and redundant sense elements.

FIG. 6E shows a radial cross-section 650 of sensor 600 in the active area according to some embodiments. In the embodiments shown in cross-section 650 only layers 610 and 620 shown in FIGS. 6A and 6B, respectively, are shown. Note from cross-section 650 that the drive windings are printed in different layers and are slightly offset from one another as are the sense windings. Again it can be seen from FIG. 6E that the pillars 650 are formed by the pillar elements 615 and 625 which are vertically aligned with one another. The size of pillars 635 and the width of the sense elements may be chosen such that the manufacturing process used to create the sensor ensure that the pillar elements are formed with sufficient accuracy on top of one another when combined into the sensor. Similarly, the sense and sense elements and drive elements should be offset from one another a sufficient amount such that there is limited or no overlap vertically between the layers. Though, the drive windings, sense elements, and pillars may be formed in any suitable way.

Figure 7A:
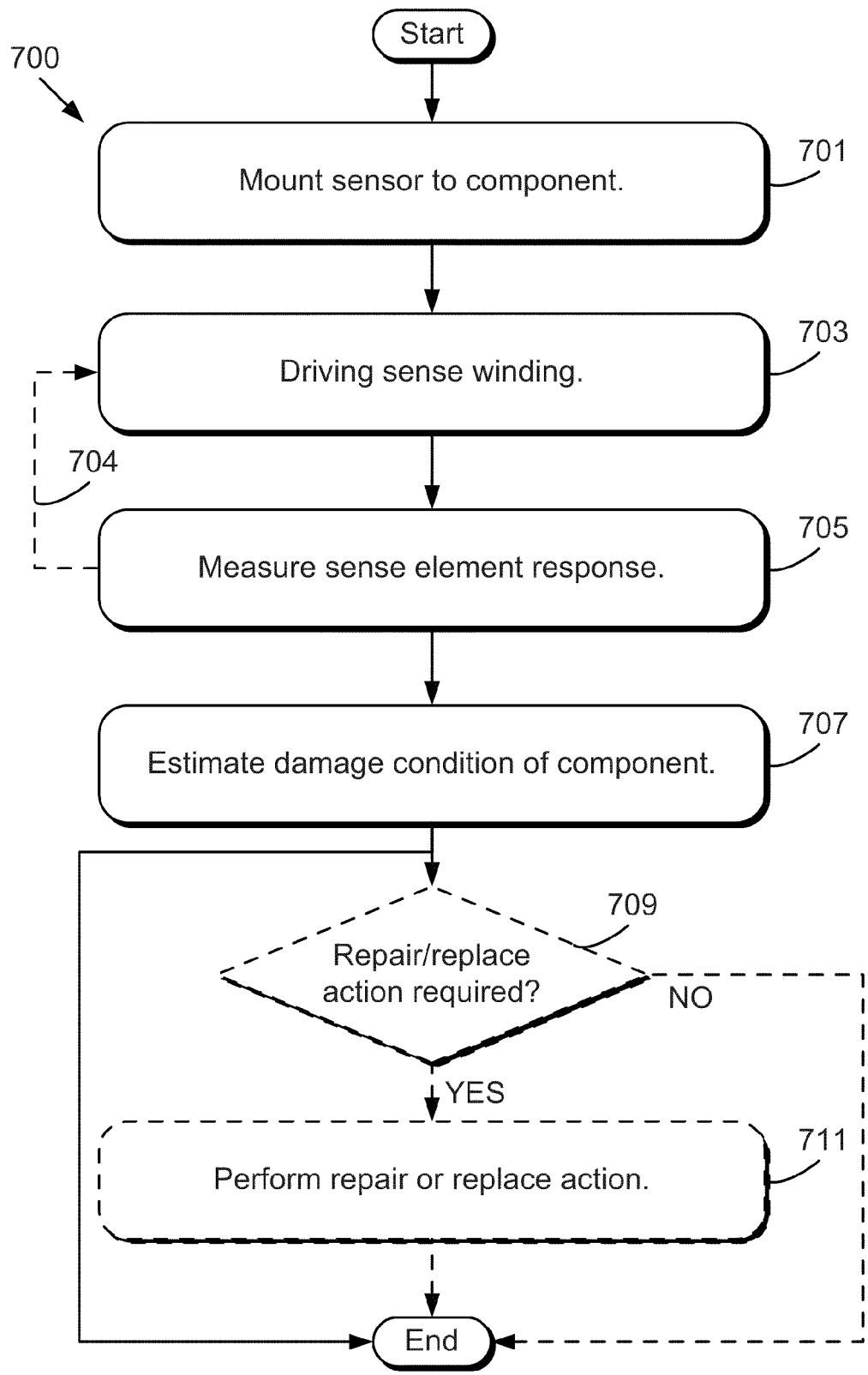
FIG. 7A illustrates a flow diagram for a method of monitoring the condition of a component under test.

Turning now to FIG. 7A, a method 700 is shown for monitoring a component with a sensor.

At step 701 the sensor is mounted to the component. In some embodiments, the sensor is an eddy-current sensor and may have features discussed above and described with reference to the drawings. For example, the sensor may be mounted at a fastener hole location on the component in ways similar to those described with reference to FIG. 1B. In some embodiments, the component may be a fuel tank.

At step 703 the drive winding of the sensor is excited by a electric current. The excitation signal may have any suitable waveform. For example, a sinusoidal signal of a selected frequency may be used as the excitation signal. The excitation signal may be generated and coupled to the drive winding in any suitable way.

At step 705 the response of the sensor's sense element is measured. In some embodiments, the terminal voltage of the sense element is measured. The measurement may be performed in any suitable way. In some embodiments, the response of multiple sense elements is measured at step 705.

As indicated by line 704, in some embodiments steps 703 and 705 are repeated one or more times. In each repetition of steps 703 and 705 the same or different excitation signals may be used. For example, the response may be measured for exciting the drive winding at a different frequency. Once the desired number of repetitions are made, method 700 may continue on to step 707.

At step 707 the damage condition of the component is estimated based on the excitation signal and the sense element response. The damage condition may be determined in any suitable way. If responses from multiple excitation signals and/or multiple sense elements were obtained, the measurements may be used alone, in combination, or both to estimate the condition of the component.

Method 700 may end after step 707 if the method is performed solely for monitoring the component. Method 700 may then be periodically repeated to continue to monitor the component and/or repeated for different excitation signals (e.g., different frequencies). Of course mounting step 701 may be bypassed unless it is determined that the sensor should be replaced or is not properly mounted.

Optionally, method 700 may include steps 709 and 711. At step 709 it is determined whether a repair or replace action is required. That is, a determination of whether the component under test needs to be repaired or replaced. In some embodiments, the determination is made based on the amount of damage. For example, in embodiments where the damage is estimate by a crack size a determination may be made whether the crack is large enough to warrant repair or replacement of the component.

If it is determined at step 709 not to perform a repair or replace action, method 700 ends. If, however, it is determined at step 709 to perform a repair or replace action at step 709, method 700 continues to step 711. At step 711 the component is repaired or replaced. For example, a fastener hole may be oversized to remove a crack growing at its surface. After step 711 method 700 ends. Method 700 may be repeated as discussed above.

A fatigue test performed in accordance with method similar to method 700. Sensor 500 (FIG. 5) was used for the test. (Note that this test was performed to demonstrate sensor durability and to relate sensor response to crack sizes. Crack size estimates were not made.) A fatigue specimen was fabricated from annealed Ti-6Al-4V. A setup similar to that shown in FIG. 1B was used, however, the component under test was a single part. Also, rather than using washers as shown in FIG. 1B, the sensor was sandwiched between the fatigue specimen and a protective Ti-6Al-4V cover plate. The function of the cover plate is to prevent shear loads from being transferred to the sensor as the fastener and nut were torqued to specific levels. The specimen was loaded into the hydraulic grips of the test machine and fatigued under tension.

In a first test a specimen without starter electrical discharge machining (EDM) notches was fatigued under constant amplitude loading for 20,000 cycles. No cracks initiated. The same sensor was transferred to a second fatigue specimen that contained an 0.016 in. EDM notch. Constant amplitude fatigue loads were applied until cracks initiated and started to grow from the EDM notch. After 997 cycles, the mean load and load amplitude were then decreased to maintain an R-ratio of 0.1 and cycling continued to extend the cracks until they extended past the sensing element (2,252 total cycles). At the end of the second fatigue test, the sensor was still completely functional.

Figure 7B:
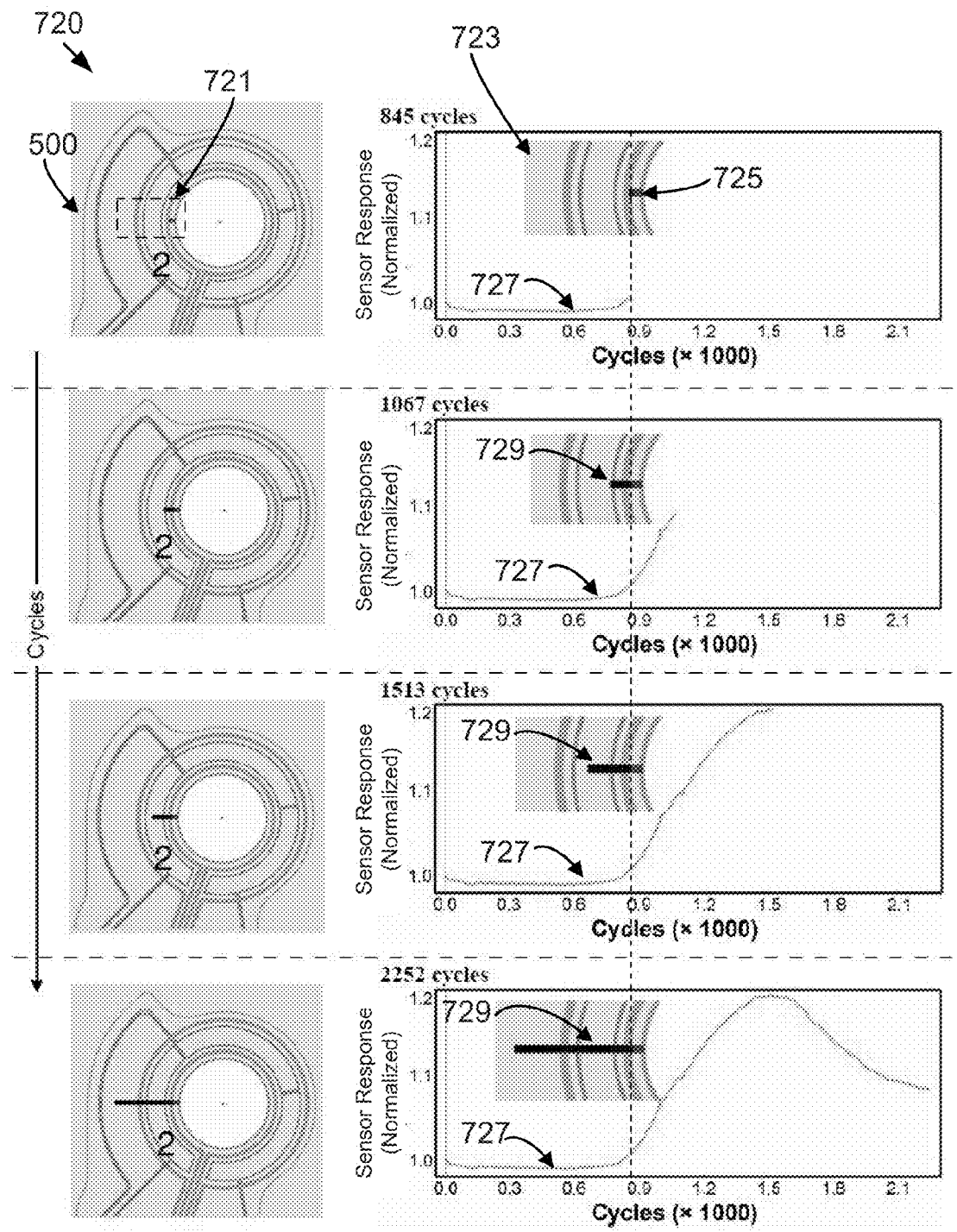
FIG. 7B shows results obtained from a sensor with durability enhancing pillars that is mounted near a bolt hole under a fatigue test.

FIG. 7B shows the progression of the sensor response on the channel which detected the initiation and growth of the fatigue crack at 845, 1067, 1,513 and 2,252 cycles. The left hand column shows a simplified illustration of sensor 500. Box 721 illustrates the location of detailed area 723. Detailed area 723 shows the location of EDM notch 725. A FASTRAN simulation was used to estimate the size of the cracks throughout the fatigue test. The FASTRAN crack estimates 729 are shown in detailed area 723 to illustrate the length of the cracks at various cycle counts throughout the test. Curve 727 shows the normalized response of the channel 2 sense element. The final crack sizes were measured using a low-power stereo microscope. For this test the number of cycles at crack initiation was assumed to occur when the sensor response began to rise. This assumption is based on previous experience.

Figure 8:
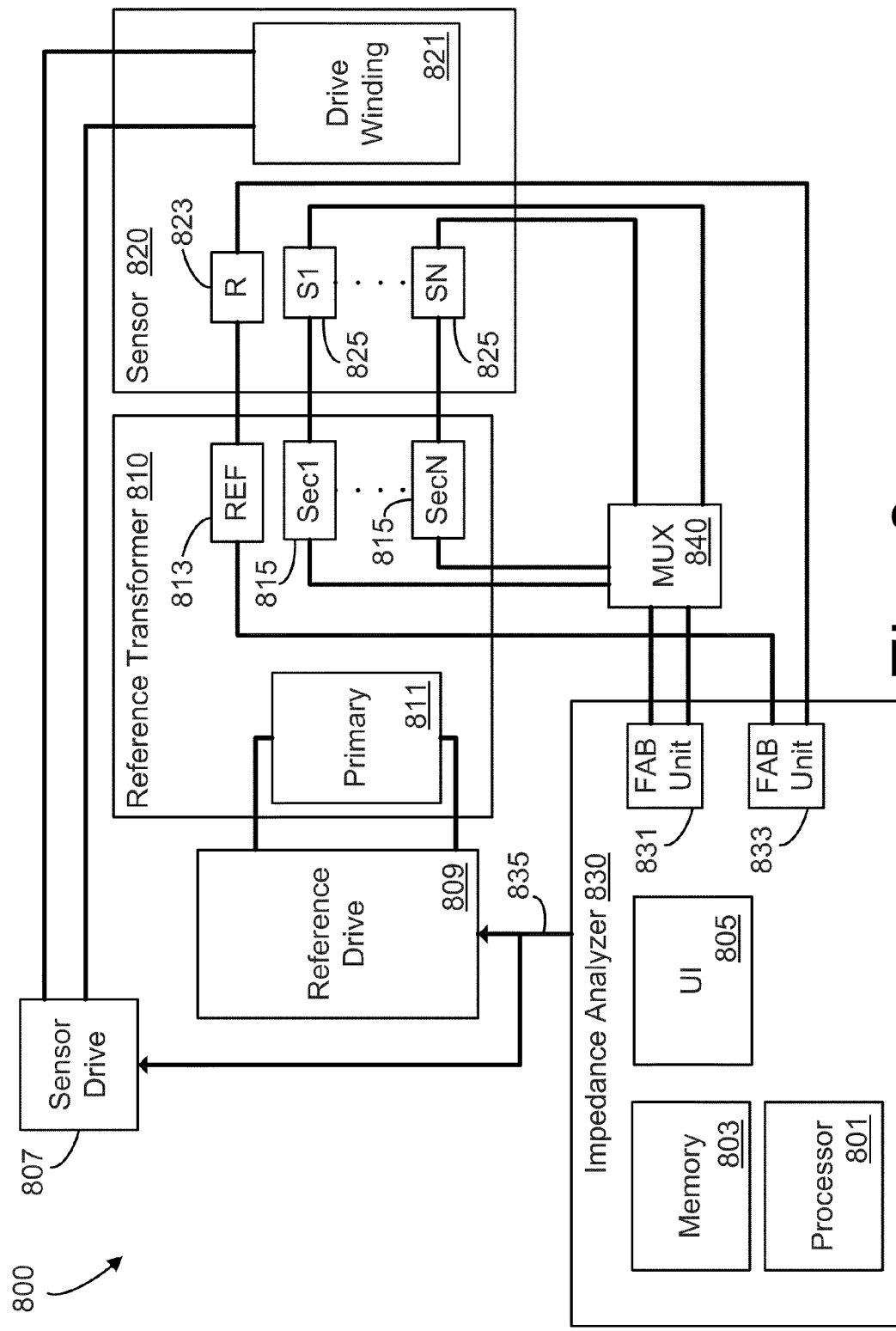
FIG. 8 is a block diagram of a system for measuring the transimpedance of the sensor using a reference transformer for calibration.

Attention is now turned to FIG. 8 which shows a system 800 for using a reference transformer 810 to calibrate the response of a sensor 820. The inventors have recognized and appreciated that in embedded sensor applications it is difficult to use conventional sensor calibration techniques such as air or reference part calibration. Such conventional techniques assume that the sensor can be placed in a known environment for calibration. Air calibration presupposes that the sensor may be located with nothing but air within its volume of sensitivity. Reference part calibration presupposes the ability to place the sensor proximal to a reference part. These techniques are impractical once a sensor has been mounted on a component to be tested. Without calibration, systematic error may drastically reduce the accuracy and reliability of sensor measurements. Calibration accounts for factors that effect the measurement that are not of interest, for example, the effect of temperature on the electronics and other changes in environment that do not wish to be monitored.

System 800 includes impedance analyzer 830, reference transformer 810 and sensor 820. Impedance analyzer 830 may be controlled by processor 801 which may be configured to execute code stored on memory 803. Processor 801 and memory 803 may be similar to processor 111 and memory 115, respectively, discussed above in connection with FIG. 1A. System 800 may be controlled by an operator through user interface 805 or in any suitable way.

Impedance analyzer 830 is configured to provide a drive signal 835 to reference drive 809 or sensor drive 807. While establishing the reference transimpedance measurements, reference drive 809 provides the drive excitation to primary 811 of reference transformer 810. In some embodiments, reference transformer 810 is an air core transformer. Though other core materials may be used. Reference transformer 810 includes one or more secondary windings 815 that are connected in series with respective sense elements 825 of sensor 820. Additionally, reference transformer 810 may have a reference secondary winding 813 connected in series with the reference element 823 of sensor 820. Though, reference element 823 may be located at other locations in the system. For example, reference element may be located in a housing inclosing reference transformer 810.

When drive signal 835 is provided by reference drive 809 on primary 811 the transimpedance is measured in part by "FAB" unit 833. FAB unit 833 provides filtering, amplification and buffering of the received signal such that, for example, a voltage may be measured for calibrating sensor 820.

Specifically, the impedance measured by FAB unit 833 is impedance across reference secondary 813 connected in series with reference 823. Similarly, while reference drive 809 provides the drive signal to primary 811 secondaries 815 which are series connected to respective sense elements 825 of sensor 820 are measured by FAB unit 831. Multiplexer 840 cycles through each of the reference secondaries 815 such that a reference value can be recorded by FAB unit 831 in each case.

Once reference transimpedance values have been measured by the impedance analyzer for the reference channel 813 and each of the secondaries 815 of reference transformer these values are recorded in memory 803. Impedance analyzer 830 then instructs sensor drive 807 to provide the excitation signal to drive winding 821 of sensor 820. As with reference transformer 810 FAB unit 831 and FAB unit 833 are used to measure the impedance for each of the series connected reference trend or secondaries 815 and sensor elements 825. Multiplexer 840 facilitates this action by cycling through each of the channels. After the raw transimpedance data is recorded by impedance analyzer 830 the prerecorded transimpedance data measured when the primary 811 of reference transformer 810 was excited are loaded from memory 803 and used to correct the raw transimpedance data measured while drive winding 821 of sensor 820 was excited. In this way robust transimpedance data can be measured with high accuracy despite environmental variables such as temperature fluctuations in the electronics of impedance analyzer 830.

The inventors have recognized and appreciated that providing a serial architecture for monitoring the impedance of a group of mounted sensors may significantly reduce the setup burden of such a network as compared to conventional techniques such as a parallel architecture or providing individual impedance instruments for each sensor. According to some embodiments, an impedance instrument is connected to a plurality of series connected multiplexing units. Each multiplexing unit is in turn connected to a respective sensor. The multiplexing units may be daisy chained using standardized cables that may be manufactures quickly and at low cost. Unlike a parallel architecture custom cabling is not needed and only suitable lengths to be selected. The multiplexing units provide some of the electronics needed for impedance measurements closer to the sensors themselves which improves the integrity of the sensor measurements that are made. Thus the overall size of the distributed group of sensors may be drastically increased. Rather than requiring all sensors to be within a few yards of one another, the serial architecture described herein permits sensors to be distributes over hundreds of yards.

Figure 9A:
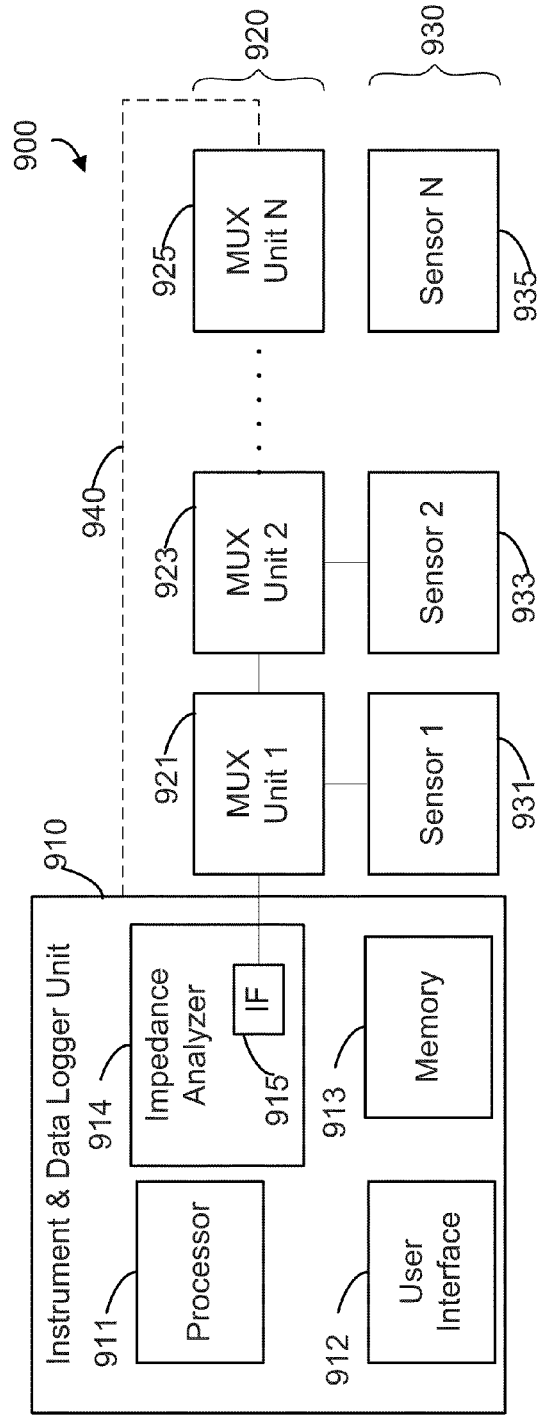
FIGS. 9A and 9B show systems for monitoring a sensor network using an impedance instrument and serially connected multiplexing units.

FIG. 9A shows a system 900 for monitoring series connected sensors 930. System 900 includes an instrument and data logger unit 910 (instrument 910). Instrument 910 are processor 911, memory 913, a user interface 912 and an impedance analyzer 914. Instrument 910 may be similar to instrument 110 described above in connection with FIG. 1A.

Impedance analyzer 914 communicates with the series connected multiplexing units 920 through interface 915. Each multiplexing unit 920 is connected to a respective sensor 930. For example, multiplexing unit 921 is connected to sensor 931, multiplexing unit 923 is connected to sensor 933 and multiplexing unit 925 is connected to sensor 935. The sensors may be each be proximate to a component under test or at multiple locations of a component.

A return path 940 from the last multiplexing unit 925 may be included to provide signal integrity for system 900. In some embodiments multiplexing unit 925 may function as a termination unit or "caboose" providing proper termination for the series connected units. Though any suitable termination may be used to provide signal integrity.

Impedance analyzer 914 provides an excitation signal and a control signal to the series connected multiplexing units 930. The control signal is used to designate which of multiplexing units 920 is to excite its respective sensor with the drive signal and provided information back to impedance analyzer 914. Specifically, multiplexing units 930 return a reference signal that characterizes the drive signal as provided to the activated sensor and one or more sense signals that characterizes the response of a sense element to the drive signal.

When a multiplexing unit (e.g., unit 923) is identified by the control signal of impedance analyzer 914 to perform measurements, the multiplexing unit provides the drive signal to the respective sensor (e.g., 933). The drive signal couples to the sense elements of the respective sensor in accordance with the properties of the sensor and the component under test. A voltage is produced on the sensor element and received by the multiplexing unit. This voltage is returned as a sense measurement to impedance analyzer 914. Similarly the drive signal may be characterize and returned to impedance analyzer 914. In some embodiments, the drive signal is passed through a resistor connected in series with the drive winding. The voltage across the resistor may then be returned to impedance analyzer 914. The resistor may be of known value such that the voltage may be related to the current through the drive winding. The combination of the sense element voltage and the current through the drive winding may be used to define a transimpedance for the sense element.

If the sensor is provided with more than one sense element the multiplexing unit may be configured to sequentially provide the sense element voltage signal back to impedance analyzer 914 through the daisy chain network.

Figure 9B:
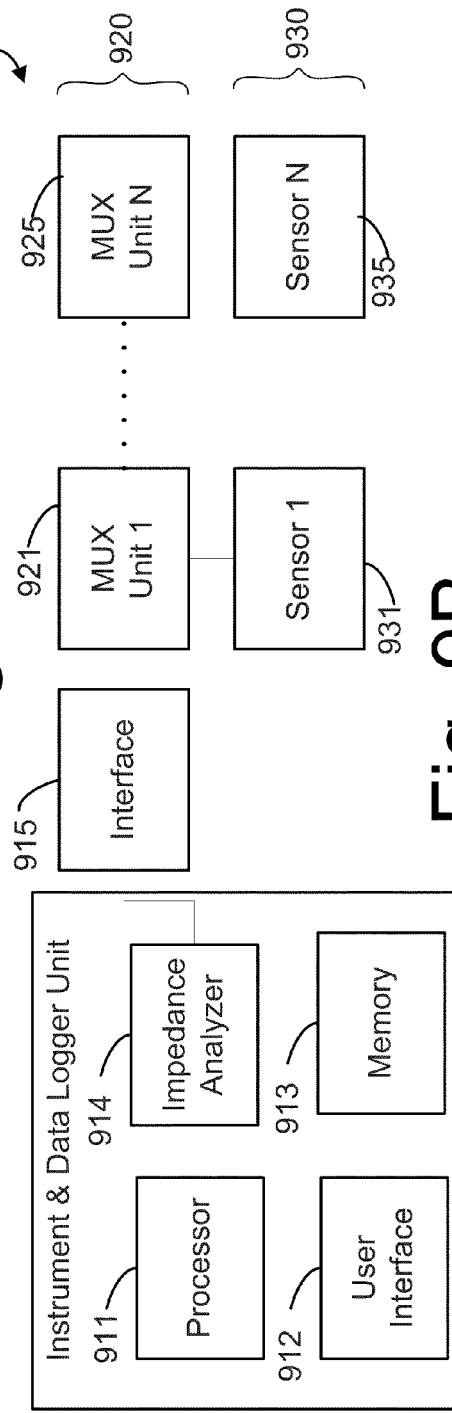

FIG. 9B shows a system 950 similar to the system 900 shown in FIG. 9A. System 950 has interface box 915 located outside of instrument 910. This configuration may be preferred in some embodiments as it moves the hardware in the interface 915 closer to the multiplexing unit. It should be appreciated that these distances could be considerable. For example, distances of 10, 100 or even 1,000 meters may be practical under this serial configuration. In comparison, conventional parallelized architecture with limit the distance between the impedance analyzer and the sensors to just a few meters. As distances increased under these conventional configurations the signal quality decreases.

Figure 9C:
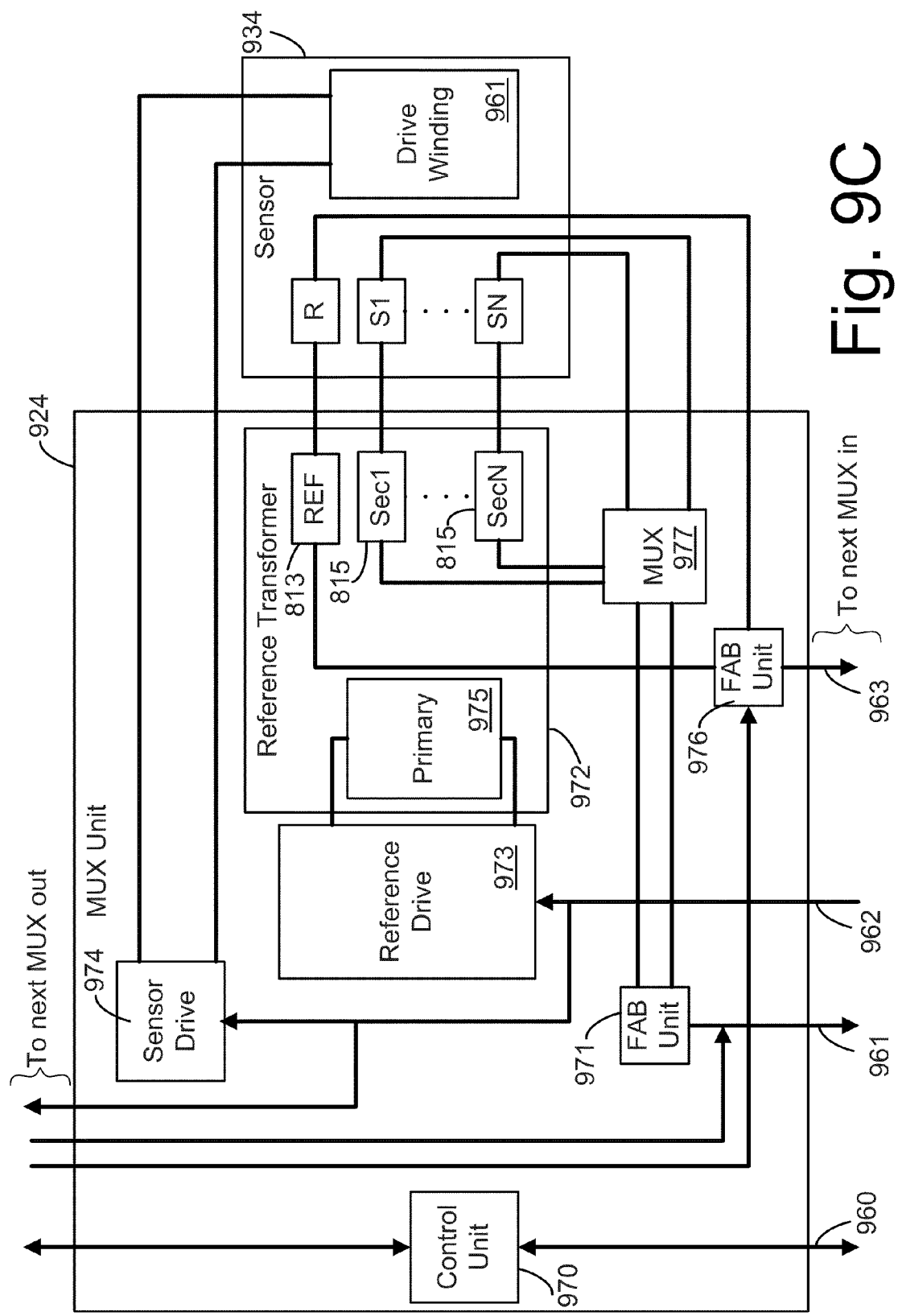
FIG. 9C is a block diagram of a multiplexing unit according to some embodiments.

FIG. 9C shows a multiplexing unit 924 according to some embodiments. This multiplexing unit is representative of any of the multiplexing units 920 in FIGS. 9A and 9B. Though, it should be appreciated that the multiplexing units need not be identical. Multiplexing unit 924 may have four serial communication channels as show in FIG. 9C. Control signal 960 is passed from the proceeding MUX unit to control unit 970 of MUX unit 920. The control signal 960 may provide information about which multiplexing unit is to currently take sensor measurements. In some embodiments, the previously described reference transformer configuration for calibration of the sensor may be integrated into the MUX unit 920. The control signal may cause control unit 970 to activate the reference drive to receive the drive signal 962 and provided on primary of reference transformer. A reference signal may then be provided to provide measurements of the reference value and similarly the sense signal may be provided from each reference transformer channel of the secondaries.

Once the reference transformer transimpedance measurements have been made, or if no reference transformer transimpedance measurements are to be made the control unit may trigger sensor drive to provide the drive signal 962 to drive winding of sensor. The MUX may then provide each of the sense element responses to the FAB unit which then passes these signals on to sense signal channel 961.

When MUX unit 920 is not the selected multiplexing unit, it simply passes these signals to and from the next multiplexing unit out on to the network. If multiplexing unit 920 is the last multiplexing unit in the series connected network the output terminals may be appropriately terminated. For example, a match load may be placed on the output terminals, a signal may be returned back to the impedance analyzer, or a caboose channel may be placed at the end of the series connected MUX.

In some embodiments, multiplexing is to locate a miniaturized impedance instrument at each sensors node and a multiplexer to switch between sensing elements. The multiplexer enables a single impedance channel to measure the response of each sensing element and a local reference transformer. The impedance response is then communicated to a central data acquisition unit. The signal may be communicated over an optical fiber network after conversion to an optical signal.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A substantially planar sensor having a first surface and a second surface, the sensor comprising:
   a drive winding configured to guide an electrical current;
   a sense element configured to couple to a magnetic field produced if the drive winding is excited with the electric current;
   a plurality of pillars configured to protect the drive winding and sense element if the first and second surfaces are under load; and
   a substrate configured to provide mechanical support to the drive winding, the sense element and the pillars,
   wherein the sensor further comprises a redundant drive winding,
   wherein the substrate is formed from a plurality of layers and the drive winding and the redundant drive winding are formed between different layers of the substrate.

2. A substantially planar sensor having a first surface and a second surface, the sensor comprising:
   a drive winding configured to guide an electrical current;
   a sense element configured to couple to a magnetic field produced if the drive winding is excited with the electric current;
   a plurality of pillars configured to protect the drive winding and sense element if the first and second surfaces are under load; and
   a substrate configured to provide mechanical support to the drive winding, the sense element and the pillars;
   wherein the drive winding comprises a substantially circular portion and the substrate has a hole in a region comprising the center of the substantially circular portion of the drive winding.

3. The sensor of claim 2, wherein:
   the drive winding has a first dimension in a direction perpendicular to the first surface of the sensor,
   the sense element has a second dimension in the direction perpendicular to the first surface of the sensor, and
   each of the plurality of pillars has a third dimension in the direction perpendicular to the first surface of the sensor, said third dimension being greater than the first dimension and greater than the second dimension.

4. The sensor of claim 2, wherein the drive winding comprises a single turn.

5. The sensor of claim 2, wherein the sensor further comprises a redundant drive winding.

6. The sensor of claim 2, wherein the sense element is among a plurality of sense elements that are each configured to couple to the magnetic field if the drive winding is excited with the electrical current.

7. The sensor of claim 2, wherein the drive winding is a first drive winding and the sensor further comprises a second drive winding having a substantially circular portion of a different radius than the substantially circular portion of the first drive winding.

8. A method of using the sensor of claim 2 to detect damage near a fastener hole of a component, the method comprising:
   mounting the sensor at the fastener hole location of the component;
   driving the sense winding to produce the electric current;
   monitoring a response of the sense element to the electric current; and
   determining a damage condition of the component from the response.

9. A substantially planar eddy current sensor having a first surface and a second surface, the sensor comprising:
   a first drive winding configured to guide a first electrical current, the first drive winding comprising a substantially circular portion having a first radius;
   a second drive winding configured to guide a second electrical current, the second drive winding comprising a substantially circular portion having a second radius greater than the first radius;

a plurality of sense elements arranged about a perimeter of the substantially circular portion of the first drive winding, each sense element configured to couple to at least one of a magnetic field produced by the first electric current and a magnetic field produced by the second electric current;

a substrate material configured to provide mechanical support to the first drive winding, the second drive winding an the plurality of sense elements; and a plurality of pillars configured to protect the drive winding and sense element if the first and second surfaces are under load, wherein the first drive winding comprises a single, substantially circular portion having a first radius and wherein the sensor further comprises a substantially circular hole concentric with the substantially circular portion of the first drive winding, the hole having a second radius less than the first radius.

10. The sensor of claim 9, wherein the plurality of sense elements are arranged outside the perimeter of the substantially circular portion of the first drive winding and the second drive winding is so positioned such that the plurality of sense elements are arranged inside a perimeter of the substantially circular portion of the second drive winding.

11. The sensor of claim 10, wherein the first drive winding and the second drive winding are connected in series.

12. A substantially planar eddy current sensor having a first surface and a second surface, the sensor comprising:

a first drive winding configured to guide a first electrical current, the first drive winding comprising a substantially circular portion having a first radius;

a second drive winding configured to guide a second electrical current, the second drive winding comprising a substantially circular portion having a second radius greater than the first radius;

a plurality of sense elements arranged about a perimeter of the substantially circular portion of the first drive winding, each sense element configured to couple to at least one of a magnetic field produced by the first electric current and a magnetic field produced by the second electric current; and a substrate material configured to provide mechanical support to the first drive winding, the second drive winding and the plurality of sense elements, wherein the plurality of sense elements are arranged outside the perimeter of the substantially circular portion of the first drive winding and the second drive winding is so positioned such that the plurality of sense elements are also arranged outside a perimeter of the substantially circular portion of the second drive winding.

13. A substantially planar eddy current sensor having a first surface and a second surface, the sensor comprising:

a first drive winding configured to guide a first electrical current, the first drive winding comprising a substantially circular portion having a first radius;

a second drive winding configured to guide a second electrical current, the second drive winding comprising a substantially circular portion having a second radius greater than the first radius;

a plurality of sense elements arranged about a perimeter of the substantially circular portion of the first drive winding, each sense element configured to couple to at least one of a magnetic field produced by the first electric current and a magnetic field produced by the second electric current; and a substrate material configured to provide mechanical support to the first drive winding, the second drive winding and the plurality of sense elements, wherein the substrate comprises a plurality of layers, the first drive winding is formed on a first layer surface and the second drive winding is formed on a second layer surface.

14. The sensor of claim 13, where the first layer surface and the second layer surface are opposite sides of a same layer among the plurality of layers of the substrate.

15. The sensor of claim 13, wherein the plurality of sense elements comprises a first subset of sense elements formed on the first layer surface, and a second subset of sense elements formed on the second layer surface.

* * * * *